(12) United States Patent
Boling et al.

(10) Patent No.: US 8,886,325 B2
(45) Date of Patent: *Nov. 11, 2014

(54) IMPLANTABLE NEUROSTIMULATOR WITH INTEGRAL HERMETIC ELECTRONIC ENCLOSURE, CIRCUIT SUBSTRATE, MONOLITHIC FEED-THROUGH, LEAD ASSEMBLY AND ANCHORING MECHANISM

(71) Applicant: Autonomic Technologies, Inc., Redwood City, CA (US)

(72) Inventors: Carl Lance Boling, San Jose, CA (US); Benjamin David Pless, Atherton, CA (US); Ryan Powell, Menlo Park, CA (US); Anthony V. Caparso, San Jose, CA (US)

(73) Assignee: Autonomic Technologies, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/939,068

(22) Filed: Jul. 10, 2013

(65) Prior Publication Data
US 2013/0296993 A1    Nov. 7, 2013

Related U.S. Application Data

(63) Continuation of application No. 12/765,712, filed on Apr. 22, 2010, now Pat. No. 8,494,641.

(60) Provisional application No. 61/171,749, filed on Apr. 22, 2009, provisional application No. 61/177,895, filed on May 13, 2009.

(51) Int. Cl.
*A61N 1/34* (2006.01)
*A61N 1/05* (2006.01)
*A61N 1/375* (2006.01)
*A61N 1/36* (2006.01)

(52) U.S. Cl.
CPC ............ *A61N 1/0526* (2013.01); *A61N 1/0546* (2013.01); *A61N 1/375* (2013.01); *A61N 1/36071* (2013.01)

USPC .......................................................... 607/46

(58) Field of Classification Search
USPC .......................................................... 607/46
See application file for complete search history.

(56) References Cited

U.S. PATENT DOCUMENTS

| 2,123,980 | A | 7/1938 | Warwick |
| 2,182,071 | A | 12/1939 | Crossley |

(Continued)

FOREIGN PATENT DOCUMENTS

| EP | 69427 A2 | 1/1983 |
| EP | 0970813 A2 | 1/2000 |

(Continued)

OTHER PUBLICATIONS

Alstadhaug, K.B.; Migraine and the hypothalamus; Cephalalgia (Blackwell Publishing Ltd.); pp. 1-9; Aug. 2009.

(Continued)

*Primary Examiner* — Eric D. Bertram
(74) *Attorney, Agent, or Firm* — Shay Glenn LLP

(57) ABSTRACT

An implantable medical device is provided for the suppression or prevention of pain, movement disorders, epilepsy, cerebrovascular diseases, autoimmune diseases, sleep disorders, autonomic disorders, abnormal metabolic states, disorders of the muscular system, and neuropsychiatric disorders in a patient. The implantable medical device can be a neurostimulator configured to be implanted on or near a cranial nerve to treat headache or other neurological disorders. One aspect of the implantable medical device is that it includes an electronics enclosure, a substrate integral to the electronics enclosure, and a monolithic feed-through integral to the electronics enclosure and the substrate. In some embodiments, the implantable medical device can include a fixation apparatus for attaching the device to a patient.

22 Claims, 16 Drawing Sheets

(56) References Cited

U.S. PATENT DOCUMENTS

| | | | |
|---|---|---|---|
| 3,357,434 A | 12/1967 | Abell | |
| 3,746,004 A | 7/1973 | Jankelson | |
| 3,859,103 A | 1/1975 | Yoshiyagawa et al. | |
| 3,862,321 A | 1/1975 | Adams et al. | |
| 3,914,283 A | 10/1975 | Okamoto et al. | |
| 3,923,060 A | 12/1975 | Ellinwood, Jr. | |
| 3,925,469 A | 12/1975 | Adams et al. | |
| 4,073,917 A | 2/1978 | Sandberg et al. | |
| 4,102,344 A | 7/1978 | Conway et al. | |
| 4,117,160 A | 9/1978 | Molnar et al. | |
| 4,147,804 A | 4/1979 | Diamond et al. | |
| 4,217,349 A | 8/1980 | Katsube et al. | |
| 4,298,603 A | 11/1981 | Chang et al. | |
| 4,305,402 A | 12/1981 | Katims | |
| 4,352,820 A | 10/1982 | Scurlock et al. | |
| 4,379,161 A | 4/1983 | Thominet et al. | |
| 4,397,845 A | 8/1983 | Allen | |
| 4,441,210 A | 4/1984 | Hochmair et al. | |
| 4,495,174 A | 1/1985 | Allcock et al. | |
| 4,519,400 A | 5/1985 | Brenman et al. | |
| 4,529,601 A | 7/1985 | Broberg et al. | |
| 4,550,733 A | 11/1985 | Liss et al. | |
| 4,551,453 A | 11/1985 | Marsili | |
| 4,565,200 A | 1/1986 | Cosman | |
| 4,592,359 A | 6/1986 | Galbraith | |
| 4,622,219 A | 11/1986 | Haynes | |
| 4,627,438 A | 12/1986 | Liss et al. | |
| 4,632,940 A | 12/1986 | Chiarino et al. | |
| 4,646,744 A | 3/1987 | Capel | |
| 4,692,147 A | 9/1987 | Duggan | |
| 4,695,576 A | 9/1987 | Ekenstam et al. | |
| 4,718,423 A | 1/1988 | Willis et al. | |
| 4,727,145 A | 2/1988 | Press | |
| 4,784,142 A | 11/1988 | Liss et al. | |
| 4,830,008 A | 5/1989 | Meer | |
| 4,833,149 A | 5/1989 | Press | |
| 4,856,526 A | 8/1989 | Liss et al. | |
| 4,870,086 A | 9/1989 | Sandberg | |
| 4,871,475 A | 10/1989 | Lubowitz et al. | |
| 4,886,493 A | 12/1989 | Yee | |
| 4,920,979 A | 5/1990 | Bullara | |
| 4,937,078 A | 6/1990 | Mezei et al. | |
| 5,038,781 A | 8/1991 | Lynch | |
| 5,085,868 A | 2/1992 | Mattsson et al. | |
| 5,178,156 A | 1/1993 | Takishima et al. | |
| 5,193,539 A | 3/1993 | Schulman et al. | |
| 5,199,428 A | 4/1993 | Obel et al. | |
| 5,215,086 A | 6/1993 | Terry, Jr. et al. | |
| 5,227,165 A | 7/1993 | Domb et al. | |
| 5,234,957 A | 8/1993 | Mantelle | |
| 5,255,691 A | 10/1993 | Otten | |
| 5,259,387 A | 11/1993 | dePinto | |
| 5,314,458 A | 5/1994 | Najafi et al. | |
| 5,330,515 A | 7/1994 | Rutecki et al. | |
| 5,335,657 A | 8/1994 | Terry, Jr. et al. | |
| 5,344,438 A | 9/1994 | Testerman et al. | |
| 5,360,805 A | 11/1994 | Ask et al. | |
| 5,387,587 A | 2/1995 | Hausler et al. | |
| 5,411,546 A | 5/1995 | Bowald et al. | |
| 5,420,151 A | 5/1995 | Hammarberg et al. | |
| 5,428,006 A | 6/1995 | Bechgaard et al. | |
| 5,433,739 A | 7/1995 | Sluijter et al. | |
| 5,458,631 A | 10/1995 | Xavier | |
| 5,490,520 A | 2/1996 | Schaefer et al. | |
| 5,514,131 A | 5/1996 | Edwards et al. | |
| 5,540,730 A | 7/1996 | Terry, Jr. et al. | |
| 5,540,734 A | 7/1996 | Zabara | |
| 5,545,219 A | 8/1996 | Kuzma | |
| 5,558,622 A | 9/1996 | Greenberg | |
| 5,560,351 A | 10/1996 | Gravenstein et al. | |
| 5,569,166 A | 10/1996 | Stone | |
| 5,578,061 A | 11/1996 | Stroetmann et al. | |
| 5,591,216 A | 1/1997 | Testerman et al. | |
| 5,640,764 A * | 6/1997 | Strojnik | 29/856 |
| 5,645,570 A | 7/1997 | Corbucci | |
| 5,653,734 A | 8/1997 | Alt | |
| 5,658,318 A | 8/1997 | Stroetmann et al. | |
| 5,660,837 A | 8/1997 | Lundquist | |
| 5,676,955 A | 10/1997 | Ansmann et al. | |
| 5,690,692 A | 11/1997 | Fleming | |
| 5,700,282 A | 12/1997 | Zabara | |
| 5,711,316 A | 1/1998 | Elsberry et al. | |
| 5,713,922 A | 2/1998 | King | |
| 5,735,817 A | 4/1998 | Shantha | |
| 5,756,520 A | 5/1998 | Ask et al. | |
| 5,766,605 A | 6/1998 | Sanders et al. | |
| 5,824,027 A | 10/1998 | Hoffer et al. | |
| 5,843,021 A | 12/1998 | Edwards et al. | |
| 5,861,014 A | 1/1999 | Familoni | |
| 5,865,843 A | 2/1999 | Baudino | |
| 5,938,688 A | 8/1999 | Schiff | |
| 6,001,088 A | 12/1999 | Roberts et al. | |
| 6,006,134 A | 12/1999 | Hill et al. | |
| 6,016,449 A | 1/2000 | Fischell et al. | |
| 6,026,326 A | 2/2000 | Bardy | |
| 6,058,331 A | 5/2000 | King | |
| 6,073,048 A | 6/2000 | Kieval et al. | |
| 6,093,145 A | 7/2000 | Vom Berg et al. | |
| 6,094,598 A | 7/2000 | Elsberry et al. | |
| 6,104,957 A | 8/2000 | Alo et al. | |
| 6,128,538 A | 10/2000 | Fischell et al. | |
| 6,132,384 A | 10/2000 | Christopherson et al. | |
| 6,134,474 A | 10/2000 | Fischell et al. | |
| 6,141,590 A | 10/2000 | Renirie et al. | |
| 6,146,380 A | 11/2000 | Racz et al. | |
| 6,161,044 A | 12/2000 | Silverstone | |
| 6,161,048 A | 12/2000 | Sluijter et al. | |
| 6,178,349 B1 | 1/2001 | Kieval | |
| 6,205,359 B1 | 3/2001 | Boveja | |
| 6,246,912 B1 | 6/2001 | Sluijter et al. | |
| 6,251,126 B1 | 6/2001 | Ottenhoff et al. | |
| 6,259,952 B1 | 7/2001 | Sluijter et al. | |
| 6,262,377 B1 | 7/2001 | Nielsen et al. | |
| 6,269,270 B1 | 7/2001 | Boveja | |
| 6,292,695 B1 | 9/2001 | Webster, Jr. et al. | |
| 6,308,105 B1 | 10/2001 | Duysens et al. | |
| 6,353,762 B1 | 3/2002 | Murthy | |
| 6,356,786 B1 | 3/2002 | Rezai et al. | |
| 6,356,787 B1 | 3/2002 | Rezai et al. | |
| 6,356,788 B2 | 3/2002 | Boveja | |
| 6,366,814 B1 | 4/2002 | Boveja et al. | |
| 6,400,982 B2 | 6/2002 | Sweeney et al. | |
| 6,405,079 B1 | 6/2002 | Ansarinia | |
| 6,432,986 B2 | 8/2002 | Levin | |
| 6,438,423 B1 | 8/2002 | Rezai et al. | |
| 6,456,786 B1 | 9/2002 | Uchida et al. | |
| 6,458,157 B1 | 10/2002 | Suaning | |
| 6,491,940 B1 | 12/2002 | Levin | |
| 6,511,500 B1 | 1/2003 | Rahme | |
| 6,526,318 B1 | 2/2003 | Ansarinia | |
| 6,564,096 B2 | 5/2003 | Mest | |
| 6,564,102 B1 | 5/2003 | Boveja | |
| 6,610,713 B2 | 8/2003 | Tracey | |
| 6,615,081 B1 | 9/2003 | Boveja | |
| 6,633,779 B1 | 10/2003 | Schuler et al. | |
| 6,647,296 B2 | 11/2003 | Fischell et al. | |
| 6,665,562 B2 | 12/2003 | Gluckman et al. | |
| 6,668,191 B1 | 12/2003 | Boveja | |
| 6,735,475 B1 | 5/2004 | Whitehurst et al. | |
| 6,760,626 B1 | 7/2004 | Boveja | |
| 6,788,975 B1 | 9/2004 | Whitehurst et al. | |
| RE38,654 E | 11/2004 | Hill et al. | |
| 6,819,956 B2 | 11/2004 | DiLorenzo | |
| 6,832,114 B1 | 12/2004 | Whitehurst et al. | |
| 6,853,858 B2 | 2/2005 | Shalev | |
| 6,885,888 B2 | 4/2005 | Rezai | |
| 6,978,180 B2 | 12/2005 | Tadlock | |
| 7,003,352 B1 | 2/2006 | Whitehurst | |
| 7,027,860 B2 | 4/2006 | Bruninga et al. | |
| 7,047,078 B2 | 5/2006 | Boggs, II et al. | |
| 7,076,307 B2 | 7/2006 | Boveja et al. | |
| 7,113,033 B2 | 9/2006 | Barnett | |
| 7,117,033 B2 | 10/2006 | Shalev et al. | |
| 7,120,489 B2 | 10/2006 | Shalev et al. | |

(56) References Cited

U.S. PATENT DOCUMENTS

| | | |
|---|---|---|
| 7,149,574 B2 | 12/2006 | Yun et al. |
| 7,167,751 B1 | 1/2007 | Whitehurst et al. |
| 7,191,012 B2 | 3/2007 | Boveja et al. |
| 7,203,548 B2 | 4/2007 | Whitehurst et al. |
| 7,209,787 B2 | 4/2007 | DiLorenzo |
| 7,277,758 B2 | 10/2007 | DiLorenzo |
| 7,285,118 B1 | 10/2007 | Lozano |
| 7,286,879 B2 | 10/2007 | Wallace |
| 7,292,890 B2 | 11/2007 | Whitehurst et al. |
| 7,340,298 B1 | 3/2008 | Barbut |
| 7,349,743 B2 | 3/2008 | Tadlock |
| 7,363,076 B2 | 4/2008 | Yun et al. |
| 7,369,897 B2 | 5/2008 | Boveja et al. |
| 7,403,821 B2 | 7/2008 | Haugland et al. |
| 7,477,945 B2 | 1/2009 | Rezai et al. |
| 7,494,458 B2 | 2/2009 | Fischell et al. |
| 7,532,938 B2 | 5/2009 | Machado et al. |
| 7,561,919 B2 | 7/2009 | Shalev et al. |
| 7,623,924 B2 | 11/2009 | Narciso, Jr. |
| 7,640,057 B2 | 12/2009 | Libbus et al. |
| 7,689,276 B2 | 3/2010 | Dobak |
| 7,763,034 B2 | 7/2010 | Siegel et al. |
| 7,778,704 B2 | 8/2010 | Rezai |
| 7,799,337 B2 | 9/2010 | Levin |
| 7,848,816 B1 | 12/2010 | Wenzel et al. |
| 7,865,237 B2 | 1/2011 | Machado et al. |
| 7,877,146 B2 | 1/2011 | Rezai |
| 8,046,075 B2 | 10/2011 | Rezai |
| 8,195,297 B2 | 6/2012 | Penner |
| 8,206,369 B2 | 6/2012 | Ansarinia |
| 8,224,438 B2 | 7/2012 | Levin |
| 8,355,779 B2 | 1/2013 | Ansarinia |
| 8,412,336 B2 | 4/2013 | Pless et al. |
| 8,473,062 B2 | 6/2013 | Pless |
| 8,489,192 B1 | 7/2013 | Hlavka et al. |
| 8,494,641 B2 | 7/2013 | Boling et al. |
| 8,583,229 B2 | 11/2013 | Rezai et al. |
| 2002/0026222 A1 | 2/2002 | Schauerte et al. |
| 2002/0073334 A1 | 6/2002 | Sherman et al. |
| 2002/0107553 A1 | 8/2002 | Hill et al. |
| 2002/0169365 A1 | 11/2002 | Nakada et al. |
| 2003/0004549 A1 | 1/2003 | Hill et al. |
| 2003/0018367 A1 | 1/2003 | DiLorenzo |
| 2003/0018368 A1 | 1/2003 | Ansarinia |
| 2003/0028147 A1 | 2/2003 | Aves et al. |
| 2003/0060857 A1 | 3/2003 | Perrson et al. |
| 2003/0065374 A1 | 4/2003 | Honeck |
| 2003/0100924 A1 | 5/2003 | Foreman et al. |
| 2003/0144709 A1 | 7/2003 | Zabara et al. |
| 2003/0176898 A1 | 9/2003 | Gross et al. |
| 2003/0181951 A1 | 9/2003 | Cates |
| 2003/0181958 A1 | 9/2003 | Dobak, III |
| 2003/0181959 A1 | 9/2003 | Dobak, III |
| 2003/0212440 A1 | 11/2003 | Boveja |
| 2003/0216792 A1 | 11/2003 | Levin et al. |
| 2004/0015204 A1 | 1/2004 | Whitehurst et al. |
| 2004/0093053 A1 | 5/2004 | Gerber et al. |
| 2004/0172084 A1 | 9/2004 | Knudson et al. |
| 2004/0230255 A1 | 11/2004 | Dobak, III |
| 2004/0236381 A1 | 11/2004 | Dinsmoor et al. |
| 2005/0038484 A1 | 2/2005 | Knudson et al. |
| 2005/0075701 A1 | 4/2005 | Shafer |
| 2005/0075702 A1 | 4/2005 | Shafer |
| 2005/0102006 A1 | 5/2005 | Whitehurst et al. |
| 2005/0143378 A1 | 6/2005 | Yun et al. |
| 2005/0143626 A1 | 6/2005 | Prescott |
| 2005/0143787 A1 | 6/2005 | Boveja et al. |
| 2005/0149156 A1 | 7/2005 | Libbus et al. |
| 2005/0153885 A1 | 7/2005 | Yun et al. |
| 2005/0154419 A1 | 7/2005 | Whitehurst et al. |
| 2005/0154426 A1 | 7/2005 | Boveja et al. |
| 2005/0159790 A1 | 7/2005 | Shalev |
| 2005/0209654 A1 | 9/2005 | Boveja et al. |
| 2005/0216070 A1 | 9/2005 | Boveja et al. |
| 2005/0234523 A1 | 10/2005 | Levin et al. |
| 2005/0281751 A1 | 12/2005 | Levin |
| 2006/0004423 A1 | 1/2006 | Boveja et al. |
| 2006/0020299 A1 | 1/2006 | Shalev |
| 2006/0064140 A1 | 3/2006 | Whitehurst et al. |
| 2006/0074450 A1 | 4/2006 | Boveja et al. |
| 2006/0074463 A1 | 4/2006 | Seeberger et al. |
| 2006/0079945 A1 | 4/2006 | Libbus |
| 2006/0085046 A1 | 4/2006 | Rezai |
| 2006/0095088 A1 | 5/2006 | De Ridder |
| 2006/0100668 A1 | 5/2006 | Ben-David et al. |
| 2006/0100671 A1 | 5/2006 | Ridder |
| 2006/0106285 A1 | 5/2006 | Boulais et al. |
| 2006/0116721 A1 | 6/2006 | Yun et al. |
| 2006/0122660 A1 | 6/2006 | Boveja et al. |
| 2006/0149337 A1 | 7/2006 | John |
| 2006/0167497 A1 | 7/2006 | Armstrong et al. |
| 2006/0173495 A1 | 8/2006 | Armstrong et al. |
| 2006/0178666 A1 | 8/2006 | Cosman et al. |
| 2006/0184211 A1 | 8/2006 | Gaunt et al. |
| 2006/0195169 A1 | 8/2006 | Gross |
| 2006/0206165 A1 | 9/2006 | Jaax et al. |
| 2006/0235484 A1 | 10/2006 | Jaax et al. |
| 2006/0287678 A1 | 12/2006 | Shafer |
| 2006/0293723 A1 | 12/2006 | Whitehurst et al. |
| 2007/0021801 A1 | 1/2007 | Heruth et al. |
| 2007/0021802 A1 | 1/2007 | Heruth et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027498 A1 | 2/2007 | Maschino et al. |
| 2007/0039625 A1 | 2/2007 | Heruth et al. |
| 2007/0049988 A1 | 3/2007 | Carbunaru et al. |
| 2007/0066997 A1 | 3/2007 | He et al. |
| 2007/0067004 A1 | 3/2007 | Boveja et al. |
| 2007/0083245 A1 | 4/2007 | Lamensdorf et al. |
| 2007/0100411 A1 | 5/2007 | Bonde |
| 2007/0106143 A1 | 5/2007 | Flaherty |
| 2007/0112404 A1 | 5/2007 | Mann et al. |
| 2007/0156177 A1 | 7/2007 | Harel et al. |
| 2007/0156179 A1 | 7/2007 | S.E. |
| 2007/0203521 A1 | 8/2007 | Dobak et al. |
| 2007/0233193 A1 | 10/2007 | Craig |
| 2007/0250119 A1 | 10/2007 | Tyler et al. |
| 2007/0250145 A1 | 10/2007 | Kraus et al. |
| 2007/0255368 A1 | 11/2007 | Bonde et al. |
| 2007/0255369 A1 | 11/2007 | Bonde et al. |
| 2007/0293906 A1 | 12/2007 | Cowan et al. |
| 2008/0027346 A1 | 1/2008 | Litt et al. |
| 2008/0033509 A1 | 2/2008 | Shalev et al. |
| 2008/0046053 A1 | 2/2008 | Wagner et al. |
| 2008/0071318 A1 | 3/2008 | Brooke et al. |
| 2008/0086182 A1 | 4/2008 | Ben-David et al. |
| 2008/0103547 A1 | 5/2008 | Okun et al. |
| 2008/0103569 A1 | 5/2008 | Gerber |
| 2008/0132933 A1 | 6/2008 | Gerber |
| 2008/0132981 A1 | 6/2008 | Gerber |
| 2008/0132982 A1 | 6/2008 | Gerber |
| 2008/0140000 A1 | 6/2008 | Shuros et al. |
| 2008/0161877 A1 | 7/2008 | Kirby et al. |
| 2008/0161894 A1 | 7/2008 | Ben-David et al. |
| 2008/0183237 A1 | 7/2008 | Errico et al. |
| 2008/0183246 A1 | 7/2008 | Patel et al. |
| 2008/0183253 A1 | 7/2008 | Bly |
| 2008/0262566 A1 | 10/2008 | Jaax |
| 2008/0269716 A1 | 10/2008 | Bonde et al. |
| 2009/0012577 A1 | 1/2009 | Rezai et al. |
| 2009/0036949 A1 | 2/2009 | Kokones et al. |
| 2009/0105783 A1 | 4/2009 | Solberg et al. |
| 2009/0118780 A1 | 5/2009 | DiLorenzo |
| 2009/0264956 A1 | 10/2009 | Rise et al. |
| 2009/0276005 A1* | 11/2009 | Pless .......................... 607/46 |
| 2009/0276025 A1 | 11/2009 | Burnes et al. |
| 2009/0312817 A1 | 12/2009 | Hogle et al. |
| 2009/0320845 A1 | 12/2009 | Fishman et al. |
| 2010/0179617 A1 | 7/2010 | Fletcher et al. |
| 2010/0185249 A1 | 7/2010 | Wingeier et al. |
| 2010/0185258 A1 | 7/2010 | Papay |
| 2010/0228316 A1 | 9/2010 | Errico et al. |
| 2010/0228318 A1 | 9/2010 | Errico et al. |

(56) References Cited

U.S. PATENT DOCUMENTS

| | | | |
|---|---|---|---|
| 2010/0268306 | A1 | 10/2010 | Maniak et al. |
| 2010/0305664 | A1 | 12/2010 | Wingeier et al. |
| 2011/0029037 | A1 | 2/2011 | Rezai et al. |
| 2011/0046432 | A1 | 2/2011 | Simon et al. |
| 2012/0209286 | A1 | 8/2012 | Papay et al. |
| 2012/0270876 | A1 | 10/2012 | Yun et al. |
| 2013/0131636 | A1 | 5/2013 | Rezai et al. |
| 2013/0178701 | A1 | 7/2013 | Pless et al. |
| 2013/0178829 | A1 | 7/2013 | Rezai et al. |

FOREIGN PATENT DOCUMENTS

| | | |
|---|---|---|
| EP | 754060 B1 | 3/2003 |
| RU | 2108817 C1 | 4/1996 |
| WO | WO85/00599 A1 | 2/1985 |
| WO | WO92/07605 A1 | 5/1992 |
| WO | WO95/21821 A1 | 8/1995 |
| WO | WO97/02000 A1 | 1/1997 |
| WO | WO97/15548 A1 | 5/1997 |
| WO | WO97/23467 A1 | 7/1997 |
| WO | WO97/38675 A1 | 10/1997 |
| WO | WO01/85094 A2 | 11/2001 |
| WO | WO01/97905 A1 | 12/2001 |
| WO | WO03/082123 A2 | 10/2003 |
| WO | WO2005/105202 A1 | 11/2005 |

OTHER PUBLICATIONS

Babe, "Treatment of sphenopalatine ganglion neuralgia", An Otorrinolaringol Ibero Am, vol. 16(5): 463-74 (year of pub. sufficiently earlier than effective US filing date and any foreign priority date) 1989 (abstract).
Barre, "Cocaine as an abortive agent in cluster headache", Headache, vol. 22: 69-73 (Mar. 1982).
Benumof et al.; Pulmonary artery catheterization; In Clinical Procedures in Anesthesia and Intensive Care; JB Lippincott Company; pp. 405-441; (year of pub. sufficiently earlier than effective US filing date and any foreign priority date) 1992.
Berger et al., "Does topical anesthesia of the sphenopalatine ganglion with cocaine or lidocaine relieve low back pain?", Anesth Analg, vol. 65(6); pp. 700-702; Jun. 1986.
Boysen et al.; Parasympathetic tonic dilatory influences on cerebral vessels; Autonomic Neuroscience: Basic and Clinical; vol. 147; pp. 101-104; Feb. 2009.
Browne et al., "Concurrent cervical and craniofacial pain" Oral Surg Oral Med Oral Path 86(6): 633-640 (Dec. 1998).
Carroll et al., "Motor cortex stimulation for chronic neuropathic pain: a preliminary study of 10 cases" Pain 84:431-437 (Feb. 2000).
Cepero et al., "Long-term results of sphenopalatine ganglioneurectomy for facial pain", Am J Otolaryngol, 8(3): 171-4 (May-Jun. 1987).
Cohen et al.; Sphenopalatine ganglion block for postdural puncture headache; Anaesthesia; vol. 64; pp. 574-575; May 2009.
Cook, "Cryosurgery of headache", Res Clin Stud Headache, vol. 5: 86-101 (year of pub. sufficiently earlier than effective US filing date and any foreign priority date) 1978 (abstract).
Cooke-Ariel; Circadian variations in cardiovascular function and their relation to the occurrence and timing of cardiac events; Am. J. Heath. Syst. Pharm.; vol. 55; supp. 3; pp. S5-S11; Nov. 15, 1998.
Cooper et al.; Neural effects on sinus rate and atrioventricular conduction produced by electrical stimulation from a transvenous electrode catheter in the canine right pulmonary artery; Circulation Research; vol. 46; pp. 48-57; Jan. 1980.
Cutrer et al., "Effects of PNU-109,291, a selective 5H-T1D receptor agonist, on electrically induced dural plasma extravasation and capsaicin-evoked c-fos immunoreactivity within trigeminal nucleus caudalis" Neuropharm 38:1043-1053 (Jul. 1999).
Delepine et al., "Plasma protein extravasation induced in the rat dura mater by stimulation of the parasympathetic sphenopalatine ganglion", Exp Neurology, vol. 147: 389-400 (Oct. 1997).

Devoghel, "Cluster headache and sphenopalatine block", Acta Anaesthesio Belg, vol. 32(1), pp. 101-107 (year of pub. sufficiently earlier than effective US filing date and any foreign priority date) 1981.
Feindel et al., "The tentorial nerves and localization of intracranial pain in man" Neurology; 10(6); pp. 555-563; Jun. 1960.
Ferrante et al., "Sphenopalatine ganglion block for the treatment of myofascial pain of the head, neck, and shoulders", Reg Anesth Pain, vol. 23(1): 30-6 (Jan.-Feb. 1998) (abstract).
Frisardi et al., "Electric versus magnetic transcranial stimulation of the trigeminal system in healthy subjects. Clinical applications in gnathology.", J Oral Rehabil, 24(12): 920-8; Dec. 1987 (abstract).
Giles; Importance of long-acting andiotensin-converting enzyme inhibitors for congestive heart failure; Am. J. Cardiol.; vol. 70; pp. 98C-101C; Oct. 8, 1992.
Goadsby et al., "Differential effects of low dose CP122,288 and eletriptan on Fos expression due to stimulation of the superior sagittal sinus in cat" Pain 82:15-22 (Jul. 1999).
Goadsby et al., "Stimulation of an intracranial trigeminally-innervated structure selectively increases cerebral blood flow" Brain Research 751:247-252 (Mar. 1997).
Goadsby et al., "Substance P blockade with the potent and centrally acting antagonist GR205171 does not effect central trigeminal activity with superior sagittal sinus stimuation" Neuroscience 86(1):337-343 (Sep. 1998).
Goadsby et al., "The trigeminovascular system and migraine: studies characterizing cerebrovascular and neuropeptide changes seen in humans and cats" Ann Neurol 33:48-56 (Jan. 1993).
Goadsby et al., Effect of stimulation of trigeminal ganglion on regional cerebral blood flow in cats; Am J. Physiol.; vol. 22; pp. R270-R274; Aug. 1987.
Goadsby, "Sphenopalatine ganglion stimulation increases regional blood flow independent of glucose utilization in the cat", Brain Research, vol. 506: 145-8 (Jan. 1990).
Gregoire, "Cluster headaches", Can Nurse, vol. 87(9): 33-5 (Oct. 1991) (abstract).
Gromova et al.; Sinusoidal modulated currents in comprehensive treatment of children with bronchial asthma; Voprosy Kurortologii Fizioterapii, I Lechebnoi Fizicheskoi Kultury; May-Jun; (3); pp. 45-47; (year of pub. sufficiently earlier than effective US filing date and any foreign priority date) 1981 (w/ English Abstract).
Grossmann; Effects of cardiac glycosides on 24-h ambulatory blood pressure in healthy volunteers and patients with heart failure; Eur J Clin Invest; vol. 31; Iss.S2; pp. 26-30; Apr. 2001.
Gudovsky et al.; Surgical treatment of bronchial asthma; Surgery (Khigurgiia); vol. 7; pp. 14-18; Jul. 2002.
Guo et al.; Treatment of primary trigeminal neuralgia with acupuncture at the sphenopalatine ganglion; Journal of traditional chinese medicine; vol. 15(1) pp. 31-33; Mar. 1995.
Hardebo, Jan-Erik; Activation of pain fibers to the internal carotid artery intracranially may cause the pain and local signs of reduced sympathetic and enhanced parasympathetic activity in cluster headache; Headache; 31; pp. 314-320; May 1991.
Hardebo, Jan-Erik; On pain mechanisms in cluster headache; Headache; 31; pp. 91-106; Feb. 1991.
Headache Classification Committee of the International Headache Society, "Classification and diagnostic criteria for headache disorders, cranial neuralgias and facial pain", Cephalalgia, Supp & 0:13, 19-24 and 35-38 (Feb. 1988).
Heusch et al.; Adrenergic mechanisms in myocardial ischemia; Supp. to Basic Research in Cardiology; vol. 85; (year of pub. sufficiently earlier than effective US filing date and any foreign priority date) 1990.
Hillier; Monitored anesthesia care; Clinical Anesthesia; Ch. 47; pp. 1239-1254; Jan. 2001.
Hoskin et al., "Fos expression in the trigeminocervical complex of the cat after stimulation of superior sagittal sinus is reduced by L-NAME" Neuroscience Letters 266:173-176 (May 1999).
Hudson; Basic principles of clinical pharmacology; Clinical Anesthesia; Ch. 11; pp. 239-260; Jan. 2001.

(56) References Cited

OTHER PUBLICATIONS

Ibarra, Eduardo; Neuromodulación del Ganglio Esfenopalation para Aliviar los Síntomas del la Cefalea en Raciomos; Boletin El Dolor; vol. 46, No. 16; pp. 12-18; (year of pub. sufficiently earlier than effective US filing date and any foreign priority date) 2007 (with English translation).

Iliff et al.; Epoxyeicosanoids as mediators of neurogenic vasodilation in cerebral vessels; Am J Physiol Heart Circ Physiol; vol. 296; pp. 1352-1363; Mar. 20, 2009.

Janes et al.; Anatomy of human extrinsic cardiac nerves and ganglia; American Journal of Cardiology; vol. 57; pp. 299-309; Feb. 1986.

Janzen et al., "Sphenopalatine blocks in the treatment of pain in fibromyalgia and myofascial pain syndrome", Laryngoscope, vol. 107(10): 1420-2 (Oct. 1997).

Karashurov et al.; Evolution of surgical treatment of bronchial asthma; Surgery (Khigurgiia); vol. 11; pp. 57-60; Nov. 1999.

Karashurov et al.; Radio frequency electrostimulation of the gangliated cord of the sympathetic nerve in patients with bronchial asthma; Surgery (Khigurgiia); vol. 1; pp. 44-46; (year of pub. sufficiently earlier than effective US filing date and any foreign priority date) 2000 (w/ English Abstract).

Karavis, "The neurophysiology of acupuncture: a viewpoint", Acupuncture in Medicine, vol. 15(1): 33-42 (May 1997).

Kim et al.; Sympathectomy: Open and Thoracoscopic; In: Surgical Management of Pain; Thieme Medical Publishers, Inc.; RD 595.5. 587; Chapter 55; Jan. 2002.

Kittrelle et al., "Cluster headache. Local anesthetic abortive agents", Arch Neurol, vol. 42(5): 496-8 (May 1985).

Kosaras et al.; Sensory innervation of the calvarial bones of the mouse; The Journal of Comparative Neurology (John Wiley & Sons); 48 pgs.; Mar. 2009.

Kudrow et al., "Rapid and sustained relief of migraine attacks with intranasal lidocaine: preliminary findings", Headache, vol. 35(2): 79-82 (Feb. 1995).

Kudrow, "Natural history of cluster headaches—part 1 outcome of drop-out patients", Headache, vol. 22: 203-6 (Sep. 1982).

Kushiku et al.; Upregulation of Immunoreactive Angiotensin II Release and Angiotensinogen mRNA Expression by High-Frequency Preganglionic Stimulation at the Canine Cardiac Sympathetic Ganglia; Circ Res.; 88; pp. 110-116; Jan. 2001.

Lambert et al.; Comparative effects of stimulation of the trigeminal ganglion and the superior sagittal sinus on cerebral blood flow and evoked potentials in the cat; Brain Research; vol. 453; pp. 143-149; Jun. 1988.

Lebovits et al., "Sphenopalatine ganglion block: clinical use in the pain management clinic", Clin J Pain, vol. 6(2): 131-6 (Jun. 1990).

Levine et al.; Central venous and pulmonary artery catheter monitoring; Critical Care Monitoring from Pre-Hospital to the ICU; pp. 145-158; Jan. 1995.

Maizels et al., "Intranasal lidocaine for treatment of migraine", JAMA, vol. 276(4): 319-21 (Jul. 1996).

Manahan et al., "Sphenopalatine ganglion block relieves symptoms of trigeminal neuralgia: a case report", Nebr Med J, vol. 81(9): 306-9 (Sep. 1996) (abstract).

Mansoor et al.; Ambulatory blood pressure monitoring: technique and application in the study of cardiac dysfunction and congestive heart failure; Congest Heart Fail; vol. 7; pp. 319-324; Nov./Dec. 2001.

Matsumoto et al.; Effective sites by sympathetic beta-andrenergic and vagal nonadrenergic inhibitory stimulation in constricted airways; Am Rev Respir Dis; vol. 132; pp. 1113-1117; Nov. 1985.

Matthey et al.; Bedside catheterization of the pulmonary artery: risks compared with benefits; In Clinical Procedures in Anesthesia and Intensive Care; JB Lippincott Company; vol. 109; pp. 826-834; Nov. 1988.

Meyer et al., "Sphenopalatine ganglionectomy for cluster headache", Arch Otolaryngol, vol. 92(5): 475-84 (Nov. 1970).

Meyerson et al.; Alleviation of Atypical trigeminal pain by stimulation of the gasserian ganglion via an implanted electrode; Acta Neurochirurgica; supp. 30; pp. 303-309; (year of pub. sufficiently earlier than effective US filing date and any foreign priority date) 1980.

Moskowitz et al., "Basic mechanisms in vascular headache" Headache 8 (4):801-815 (Nov. 1990).

Moskowitz, Michael; Cluster headache: evidence for a pathophysiologic focus in the superior pericarotid cavernous sinus plexus; Headache; vol. 28; pp. 584-586; Oct. 1988.

Moskowitz; Neurogenic inflammation in the pathophysiology and treatment of migraine; Neurology; vol. 43; suppl. 3; pp. S16-S20; Jun. 1993.

Murphy et al.; Human cardiac nerve stimulation; The Annals of Thoracic Surgery; vol. 54; p. 502; Sep. 1992.

Narouze et al.; Sphenopalatine ganglion radiofrequency ablation for the management of chronic cluster headache; Headache; vol. 49; pp. 571-577; Apr. 2009.

Narouze et al.; Sphenopalatine ganglion stimulation for the acute treatment of intractable migraine; American Academy of Pain Medicine Annual Meeting Abstracts; pp. 226 (Abstract No. 157); Jan. 2009.

Nguyen et al., "Chronic motor cortex stimulation in the treatment of central and neuropathic pain. Correlations between clinical, electrophysiological and anatomical data" Pain 82:245-251 (Sep. 1999).

Onofrio et al., "Surgical treatment of chronic cluster headache", Mayo Clin Proc, vol. 61(7), pp. 537-544 (Jul. 1986).

Panina et al.; Assessment of autonomic tone over a 24-hour period in patients with congestive heart failure: relation between mean heart rate and measures of heart rate variability; Am. H. J.; vol. 129; pp. 748-753; Apr. 1995.

Peterson et al., "Sphenopalatine ganglion block: a safe and easy method for the management of orofacial pain", Cranio, vol. 13(3): 177-81 (Jul. 1995) (abstract).

Phebus et al., "The non-peptide NK-1 receptor antagonist LY303870 inhibits neurogenic dural inflammation in guinea pigs" Life Sciences 60(18):1553-1561 (Mar. 1997).

Pollock et al., "Stereotactic radiosurgical treatment of sphenopalatine neuralgia", J Neurosurg, vol. 87(3): 450-3 (Sep. 1997).

Rao et al., "Effectiveness of temporal pattern in the input to a ganglion: Inhibition in the cardiac ganglion of spiny lobsters", J of Neurobiology, vol. 1, No. 2, pp. 233-245 (year of pub. sufficiently earlier than effective US filing date and any foreign priority date) 1969 (abstract).

Reder et al., "Sphenopalatine ganglion block in treatment of acute and chronic pain", Diagnosis and treatment of chronic pain, John Wright, publisher, 97-108 (year of pub. sufficiently earlier than effective US filing date and any foreign priority date) 1982.

Reuter et al.; Experimental models of migraine; Funct Neurol; suppl. 15; pp. 9-18; (year of pub. sufficiently earlier than effective US filing date and any foreign priority date) 2000.

Ruskin, "Contributions to the study of the sphenopalatine ganglion", Laryngoscope, vol. 35(2): 87-108 (Feb. 1925).

Ruskin; Sphenopalatine (nasal) gaglion: remote effects including "psychosomatic" symptons, rage reaction, pain, and spasm; Arch Phys Med Rehabil; vol. 60; pp. 353-359; Aug. 1979.

Ryan et al., "Sphenopalatine ganglion neuralgia and cluster headache: comparisons, contrasts, and treatment", Headache, vol. 17: 7-8 (Mar. 1977).

Saade et al., "Patient-administered sphenopalatine ganglion block", Reg Anesth, vol. 21(1): 68-70 (Jan.-Feb. 1996) (abstract).

Sanders et al., "Efficacy of sphenopalatine ganglion blockade in 66 patients suffering from cluster headache: a 12- to 70-month follow-up evaluation", J Neurosurg., vol. 87(6), pp. 876-880 (Dec. 1997).

Scherlag et al.; Endovascular stimulation within the left pulmonary artery to induce slowing of heart rate and paroxysmal atrial fibrillation; Cardiovascular Research; vol. 54; pp. 470-475; May 2002.

Schulz et al., "Localization of epileptic auras induced on stimulation by subdural electrodes" Epilepsia 38(12) 1321-1329 (Dec. 1997).

(56) References Cited

OTHER PUBLICATIONS

Scott et al.; Trigger point injections for chronic non-malignant musculoskeletal pain: a systematic review; Pain Medicine; vol. 10; No. 1; pp. 54-69; Jan. 2009.

Seylaz et al., "Effect of stimulation of the sphenopalatine ganglion on cortical blood flow in the rat", J Cerebr Blood Flow and Metab, vol. 8: 875-8 (Dec. 1988).

Shuster et al., "Treatment of vasomotor rhinitis, trigeminal neuralgia and Sluder's syndrome by irradiation of the sphenopalatine ganglion with helium-neon lasers", Vestin Otorinolaringol, vol. 4: 35-40 (Jul.-Aug. 1988).

Sinkjaer et al., "Electroneurography", Encyclopedia of Medical Devices and Instrumentation, Second Edition: pp. 109-132 (Apr. 2006).

Sluder, "The syndrome of sphenopalatine ganglion neuralgia", Am J Medicament Sci, vol. 111: 868-878 (year of pub. sufficiently earlier than effective US filing date and any foreign priority date) 1910.

Sluder; The anatomical and clinical relations of the sphenopalatine (Meckel's) ganglion to the nose and its accessory sinuses; NY Med. J.; vol. 90; pp. 293-298; Aug. 1909.

Steude; Percutaneous electro stimulation of the trigeminal nerve in patients with atypical trigeminal neuralgia; Neurochirurgia; vol. 21; pp. 66-69; Mar. 1978.

Storer et al., "Microiontophoretic application of serotonin (5HT) 1B/1D agonists inhibits trigeminal cell firing in the cat" Brain 120:2171-2177 (Dec. 1997).

Strassman et al., "Sensitization of meningeal sensory neurons and the origin of headaches" Nature 384:560-563 (Dec. 1996).

Suzuki et al., "Selective electrical stimulation of postganglionic cerebrovascular parasympathetic nerve fibers originating from the sphenopalatine ganglion enhances cortical blood flow in the rat", J Cerebr Blood Flow and Metab, vol. 10: 383-391 (May 1990).

Suzuki et al.; Trigeminal fibre collaterals storing substance P and calcitonin gene-related peptide ; Neuroscience; vol. 30; No. 3; pp. 595-604; (year of pub. sufficiently earlier than effective US filing date and any foreign priority date) 1989.

Taub et al., "Chronic electrical stimulation of the gasserian ganglion for the relief of pain in a series of 34 patients", J Neurosurg, vol. 86: 197-202 (Feb. 1997).

Teerlink et al.; Hemodynamic variability and circadian rhythm in rats with heart failure: role of locomotor activity; Am. J. Physiol.; vol. 264; pp. H2111-H2118; Jun. 1993.

The Cleveland Clinic Foundation; Thalamic Stimulation and Trigeminal Neuralgia; Neuroscience Pathways; Mar. (Spring) 1998 newsletter; pp. 1-2.

Theodosopoulos et al.; Endoscopic approach to the infratemporal fossa: anatomic study; Neurosurgery; vol. 66; No. 1; pp. 196-203; Jan. 2010.

Toda et al.; Cerebral blood flow regulation by nitric oxide: recent advances; Pharmacol Rev; vol. 61; No. 1; pp. 62-97; Mar. 2009.

Van Horne et al.; Multichannel semiconductor-based electrodes for in vivo electrochemical and electrophysiological studies in rat CNS; Neuroscience Letters; vol. 120; pp. 249-252; Nov. 1990.

Vitek; Mechanisms of deep brain stimulation: excitation or inhibition; Movement Disorders; vol. 17; supp. 3; pp. S69-S72; Mar.-Apr. 2002.

Walters et al.; Cerebrovascular projections from the sphenopalatine and otic ganglia to the middle cerebral artery of the cat; Stroke; vol. 17; pp. 488-494; May-Jun. 1986.

Witte et al.; Experimental heart failure in rats: effects on cardiovascular circadian rhythms and on myocardial ?-adrenergic signaling; Cardiovasc Res; vol. 47; pp. 350-358; Aug. 2000.

Yee et al.; Circadian variation in the effects of aldosterone blockade on heart rate variability and QT dispersion in congestive heart failure; J. Am. Coll. Cardiol.; vol. 37; pp. 1800-1807; Jun. 2001.

Young, "Electrical stimulation of the trigeminal nerve root for the treatment of chronic facial pain", J Neurosurg, vol. 83: 72-78 (Jul. 1995).

Zarembinski et al.; Sphenopalatine ganglion block in traumatic trigeminal neuralgia and the outcome to radiosurgical ablation; American Academy of Pain Medicine Annual Meeting Abstracts; pp. 200 (abstract No. 102); Jan.-Feb. 2009.

Boling et al.; U.S. Appl. No. 14/223,765 entitled "Implantable Neurostimulator with Integral Hermetic Electronic Enclosure, Circuit Substrate, Monolithic Feed-Through, Lead Assembly and Anchoring Mechanism," filed Mar. 24, 2014.

\* cited by examiner

IMPLANTABLE NEUROSTIMULATOR WITH INTEGRAL HERMETIC ELECTRONIC ENCLOSURE, CIRCUIT SUBSTRATE, MONOLITHIC FEED-THROUGH, LEAD ASSEMBLY AND ANCHORING MECHANISM

CROSS-REFERENCE TO RELATED APPLICATIONS

This application is a continuation of U.S. application Ser. No. 12/765,712, filed Apr. 22, 2010, now U.S. Pat. No. 8,494,641, which application claims the benefit under 35 U.S.C. 119 of U.S. Provisional Application No. 61/171,749, filed Apr. 22, 2009, and U.S. Provisional Application No. 61/177,895, filed May 13, 2009. These applications are herein incorporated by reference in their entirety.

FIELD OF THE INVENTION

The invention relates generally to a stimulating apparatus used to deliver electrical stimulation to a peripheral, central or autonomic neural structure. More specifically, the current invention relates to a neurostimulator apparatus designed to deliver electrical stimulation to the sphenopalatine ganglion (SPG) to treat primary headaches, such as migraines, cluster headaches and/or many other neurological disorders, such as atypical facial pain and/or trigeminal neuralgias.

BACKGROUND OF THE INVENTION

Electrical stimulation of peripheral, central and autonomic neural structures have shown increased interest due to the potential benefits it may provide to individuals suffering from many neurological and behavioral diseases. Many of these therapies today are not well accepted or are considered last in the therapeutic options due to the invasive nature of the therapy even though the efficacy may be quite good. This has created a need for less invasive therapies that are directed toward patient and physician clinical needs.

Primary headaches are one of the most debilitating ailments that afflict millions of individuals worldwide. The specific pathophysiology of headaches is unknown. Known sources of headache pain consist of trauma, vascular, autoimmune, degenerative, infectious, drug and medication-induced, inflammatory, neoplastic, metabolic-endocrine, iatrogenic, musculoskeletal and myofacial causes. Also, even though the possible underlying cause of the headache pain is identified and treated, the headache pain may persist.

Currently, the sphenopalatine (pterygopalatine) ganglion (SPG) is a target of manipulation in clinical medicine to treat headaches. The SPG is a large extra cranial parasympathetic ganglion. It consists of parasympathetic neurons that innervate (in part) the middle cerebral and anterior cerebral blood vessels, the facial blood vessels, and the lacrimal glands. A ganglion is a mass of nervous tissue found in some peripheral and autonomic nerves. Ganglia are located on the roots of the spinal nerves and on the roots of the trigeminal nerve. Ganglia are also located on the facial, glossopharyngeal, vagus and vestibulochoclear nerves. The SPG is a complex neural ganglion with multiple connections, including autonomic, sensory and motor. The maxillary branch of the trigeminal nerve and the nerve of the pterygoid canal, also known as the vidian nerve, which is formed by the greater and deep petrosal nerves send neural projections to the SPG. The fine branches from the maxillary nerve (pterygopalatine nerves) form the sensory component of the SPG, and these fibers pass through the SPG and do not synapse. The greater petrosal nerve carries the preganglionic parasympathetic axons from the superior salivary nucleus, which is located in the Pons, to the SPG. These fibers synapse onto the postganglionic neurons within the SPG. The deep petrosal nerve connects the superior cervical sympathetic ganglion to the SPG and carries postganglionic sympathetic axons that again pass through the SPG without any synapses.

The sphenopalatine ganglion (SPG), also called the pterygopalatine ganglion, is located within the pterygopalatine fossa. The pterygopalatine fossa (PPF) is bounded anteriorly by the maxilla, posteriorly by the medial plate of the pterygoid process and greater wing of the sphenoid process, medially by the palatine bone, and superiorly by the body of the sphenoid process. Its lateral border is the pterygomaxillary fissure (PMF), which opens to the infratemporal fossa.

Treatment of the SPG is mostly performed in attempted treatments of severe headaches, such as cluster headaches or chronic migraines. Various clinical approaches have been used for over 100 years to modulate the function of the SPG to treat headaches. These procedures vary from least invasive (e.g., transnasal anesthetic blocks) to much more invasive (e.g., surgical ganglionectomy) as well as procedures such as surgical anesthetic injections, ablations, gamma knife and cryogenic surgery. Most of these procedures have very good short term efficacy outcomes (days to months), however these results are usually temporary and the headache pain returns. A chronically implanted neurostimulator apparatus designed to deliver electrical stimulation to the SPG may provide much better long term efficacy in these patients. This application details the design of a neurostimulator for this purpose.

SUMMARY OF THE INVENTION

In some embodiments, an implantable medical device configured for delivery of electrical stimulation to the Sphenopalatine Ganglion (SPG) is provided, comprising an electronics enclosure, a substrate integral to the electronics enclosure, and a monolithic feed-through integral to the electronics enclosure and the substrate.

In some embodiments, the device further comprises a fixation apparatus integral to the electronics enclosure. The fixation apparatus can comprise at least one preformed hole configured to accept a bone screw. In some embodiments, the fixation apparatus is malleable and configured to be formed around the zygomaticomaxillary buttress.

In some embodiments, the electronics enclosure comprises an ASIC, an inductive coil, and a diode array.

In some embodiments, the implantable medical device is sized and configured for implantation into the pterygopalatine fossa. In other embodiments, the implantable medical device is sized and configured for implantation on the posterior maxilla.

In one embodiment, the device further comprises a stimulation lead coupled to the electronics enclosure. The stimulation lead can be constructed to an angle off an axis of the electronics enclosure. In some embodiments, the angle is approximately 0 to 60 degrees. In other embodiments, the angle is approximately 30 degrees.

In one embodiment, the implantable medical device is configured to lay flat against the posterior maxilla, and the stimulation lead is angled so as to maintain contact with the posterior maxilla as it extends to the pterygopalatine fossa.

In another embodiment, the stimulation lead is sized and configured to pass through a lateral opening of the pterygopalatine fossa. In some embodiments, a diameter of the stimulation lead is approximately 2-12 mm.

In one embodiment, the device can further comprise at least one electrode disposed on the stimulation lead. The device can further comprise at least one electrode wire coupling the at least one electrode to the electronics enclosure.

In some embodiments, the device further comprises a platinum/iridium tubing configured to connect the at least one electrode wire to the monolithic feed-through. In some embodiments, the platinum/iridium tubing comprises at least one witness hole.

In another embodiment, the device comprises a thin-film flex circuit configured to connect the at least one electrode wire to the monolithic feed-through. In another embodiment, a protrusion feature is disposed on the monolithic feed-through.

Some embodiments of the device further comprise an inductive coil configured to receive power and communication from an external controller at a depth of approximately 1-3 cm.

In some embodiments, the electronics enclosure comprises an ASIC printed on the electronics enclosure. Another embodiment further comprises at least one annular ring coupled to the electronics enclosure and configured to receive exposed ends of the monolithic feed-through.

Another embodiment of the device further comprises a stiffening mechanism configured to increase the linear stiffness of the stimulation lead. In some embodiments, the stiffening mechanism comprises a malleable wire. In other embodiments, the stiffening mechanism comprises a coiled wire. In yet another embodiment, the stiffening mechanism comprises a tapered supporting wire.

An implantable stimulator configured for delivery of electrical stimulation to a nerve is provided, comprising a housing, an electronics enclosure disposed on or in the housing, and a stimulation lead coupled to the electronics enclosure, the stimulation lead including a malleable wire configured give the stimulation lead rigidity to penetrate tissue and malleability to conform to a target anatomy.

In some embodiments, the stimulator comprises an attachment plate coupled to the housing, the attachment plate configured to accept a bone screw for attachment to bone.

DETAILED DESCRIPTION OF THE INVENTION

Figure 1:
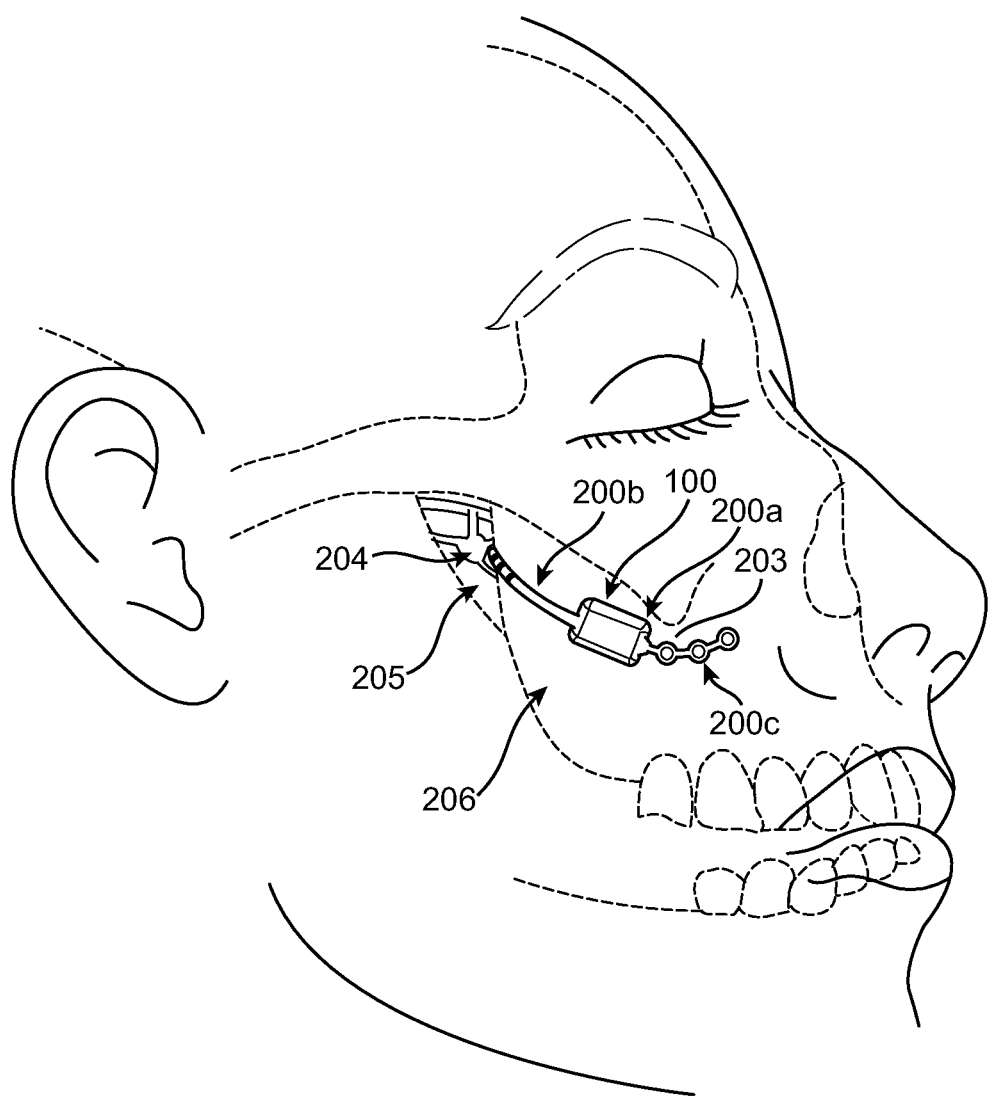
FIG. 1 is a lateral view the neurostimulator in communication with the anatomy.

Referring to FIG. 1, a neurostimulator 100 is shown within the intended anatomy for the treatment of primary headaches and other neurological disorders. The neurostimulator of this embodiment comprises of a stimulator body 200a, an integral stimulation lead 200b, and an integral fixation apparatus 200c. The neurostimulator 100 can be implanted such that the stimulator body 200b is positioned medial to the zygoma 205 on the posterior maxilla 206 within the buccal fat pad of the cheek, and the integral fixation apparatus 200c is anchored to the zygomaticomaxillary buttress 203, such as by using standard craniomaxillofacial bone screws, for example. The integral stimulation lead 200c can be placed within the pterygopalatine fossa 202, or more specifically, in very close proximity to the sphenopalatine ganglion 204.

Figure 2:
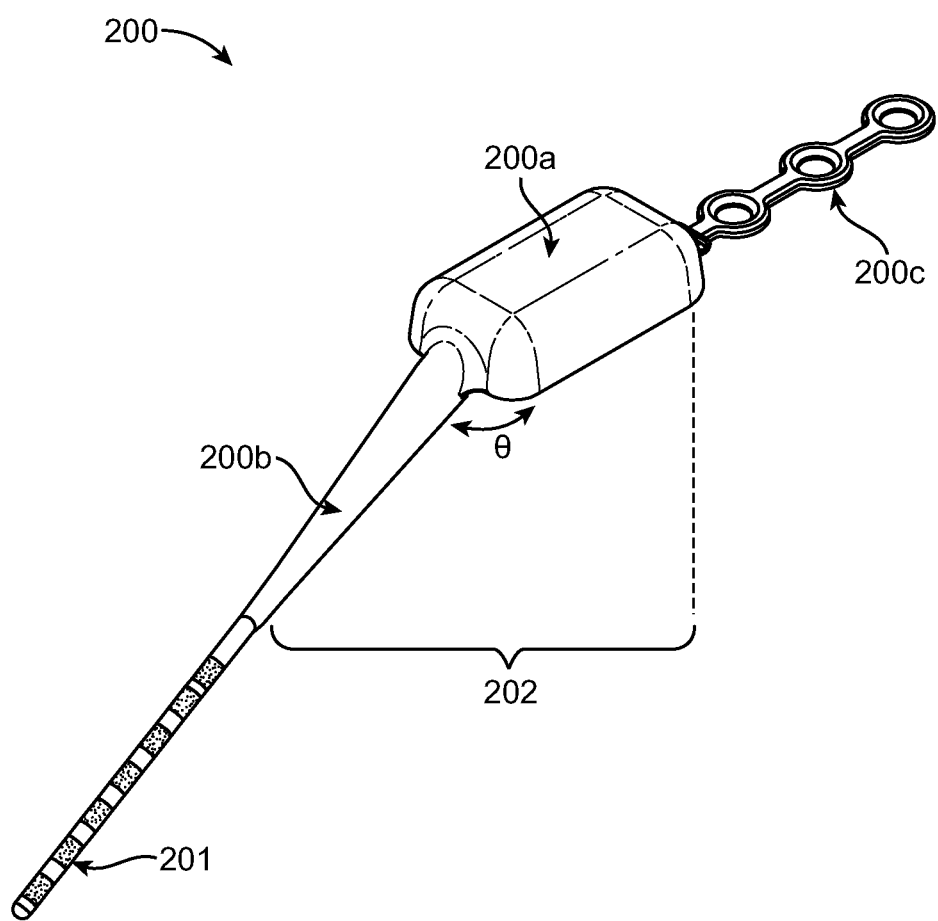
FIG. 2 is an isometric view of the neurostimulator.

FIG. 2 illustrates one embodiment of an implantable neurostimulator 200. In this embodiment, the neurostimulator 200 comprises of a stimulator body 200a, an integral stimulation lead 200b, which includes one or more stimulating electrodes 201, and an integral fixation apparatus 200c. The neurostimulator 200 of this embodiment can be an inductively powered device having the necessary micro-electronics to store programmable stimulation parameters, deliver electrical stimulation per the programmed parameters and to allow bi-directional telemetry to enable communication with an external controller. An external transmitter (not shown) provides powers to and communications with the implanted neurostimulator.

The neurostimulator's micro-electronics can be housed in the stimulator body 200a, a hettnetic enclosure that protects the micro-electronics from fluid ingress when implanted within the body. The stimulator body can further include an electronics enclosure, a micro-electronics assembly, a monolithic feed-through assembly, and a lead interconnect assembly, and the stimulator body can be molded with a protective outer layer. In some embodiments the dimensions of the stimulator body are 8 mm wide, 4 mm thick, and 14 mm long.

The neurostimulator is sized and configured to be implanted on the posterior maxilla, so the neurostimulator thickness is limited by the available free space between the posterior maxilla and the coronoid process of the mandible. The average distance between the posterior maxilla and the coronoid process, measured from 79 patients using computed tomography, was 13±3 mm with a range of 6-24 mm (unpublished work). Thus, in some embodiments the thickness of the neurostimulator can range from 1 to 10 mm. The width and length of the neurostimulator are also limited by the surrounding anatomy, but in some embodiments the width and length are such that the neurostimulator maintains physical contact with the posterior maxilla. Thus, the neurostimulation width can range from 1-20 mm, and the length can range from 1-25 mm.

Electrical stimulation can be carried from the micro-electronics to one or more of the stimulating electrodes 201 through the stimulation lead 200b. The stimulation lead can be connected to the stimulator body through a series of feed-through assemblies. In the embodiment of FIG. 2, the stimulator body 200a and a portion of the stimulating lead 200b are shown with a biocompatible outer layer 202, created using a reaction injection molding (RIM) process, to protect the feed-through assemblies, provide strain relief to the stimulation lead and create an isodiametric neurostimulator. The neurostimulator is isodiametric because the size is maintained or decreases from the most proximal portion of the stimulator body to the most distal portion of the stimulating lead. In addition, the configuration of the outer layer does not contain any sharp corners or edges. This allows the neurostimulator to be implanted and explanted without grabbing or tearing of surrounding tissue. In some embodiments, the outer protective layer is created from biocompatible urethane and silicone co-polymer. The protective layer can be up to 1 mm thick, however in some embodiments the protective layer can be 0.1 to 2 mm thick. In other embodiments, different encapsulations methods and materials may be used, including but not limited to, potting, injection molding, casting, conformal coating, or adhering a compliant, semi-compliant, or rigid silicone rubber, epoxy, thermo-set or thermoplastic polymers or combination of any of the described methods and materials around the electronic assembly, lead interconnect, and lead assembly.

Also referring to FIG. 2, the integral fixation apparatus 200c can include a biocompatible mini-plate with one or more preformed holes extending off the body of the neurostimulator. The preformed holes can be designed to accept a standard bone screw. For example, the preformed holes can be approximately 1.9 mm in diameter and be sized to accept a standard bone screw with a diameter between 1.5-1.8 mm. The preformed holes can also be designed with a ninety-degree chamfer that allows the head of the standard bone screw to recess into the mini-plate and reside flush with the outboard face of mini-plate. In one embodiment the mini-plate is made from titanium (grade 2), which provides both good mechanical fatigue resistance and good flexibility. However, in other embodiments, the mini-plate can be made from other materials such as: commercially pure titanium such as grades 1, 3, or 4 and alloys such as grade 5 or 23; stainless steels such as 304 or 316; other biocompatible metals; and biocompatible plastics such as PEEK, nylon, or polypropylene.

Additionally, as shown in FIG. 2 the one or more preformed holes are set in a linear configuration off the proximal end of the stimulator body to increase the flexibility of the mini-plate. In the intended target anatomy, the mini-plate can be anchored to the thick dense bone of the zygomatic process of the maxilla, generally referred to the zygomaticomaxillary buttress. When the stimulator body is positioned on the posterior maxilla, the mini-plate must be formed around the buttress without adversely moving or dislodging the stimulator body and the stimulation lead. Thus, the mini-plate must be malleable so that it can be formed around the buttress as well as resistant to flex fatigue from repeat bending. In one embodiment, in which the mini-plate is made from titanium (grade 2), the center-to-center distance between each of the preformed holes can be 6 mm, and the width of the beam between each preformed hole can be 1.3 mm. In this embodiment, the mini-plate provides the proper amount of malleability and flex resistance needed to form the mini-plate around the buttress and to allow for long term reliability for the chronic implantable neurostimulator. Also, the second moment of area across the mini-plate is designed to be constant, which facilitates uniform bending and typically creates a larger more uniform arch. The larger arch that is formed from bending of the mini-plate helps to resist stress concentrations and promotes matching of the surface of the mini-plate to the underlying anatomical bone features. In other embodiments, the center-to-center distance between each of the preformed holes can be between 3-10 mm and the width of the beam between each preformed hole can be 0.5 to 3 mm.

Additionally, in another embodiment, the arrangement of the preformed holes on the mini-plate can be configured into a Y configuration (a single mini-plate extending off the stimulator body with two tails extending out like a Y), a T configuration (a single mini-plate formed into a T), an L configuration (a single mini-plate formed into an L) or an X configuration (a single mini-plate formed into a X, with one leg of the X attached to the stimulator body). In any of these configurations, each of the mini-plates can contain one or more preformed holes and include the same features described above. In additional embodiments, the neurostimulator can include one or more mini-plates projecting off the stimulator body, including but not limited to a mini-plate extending off the opposing end of the stimulator body from the stimulating lead, and one or more mini-plates extending off the two other adjacent sides of the neurostimulator.

FIG. 2 also illustrates the stimulating lead 200b of neurostimulator 200. In this embodiment, the stimulating lead comprises of one or more stimulation electrodes 201 and a corresponding number of connecting lead wires for each of the stimulating electrodes. Each connecting lead wire connects to a feed-through on the stimulating lead body. The connecting wires provide a conduit to deliver electrical stimulation pulses between the micro-electronics and the stimulating electrodes. In one embodiment, the stimulation lead projects from the distal face of the stimulator body constructed to an angle of 30 degrees off the stimulator axis. In this embodiment, the inboard planer side of the neurostimulator body is configured to lay flat against and in interment communication with the posterior maxilla, which also coincides with the stimulator surface from which the integral fixation apparatus 200c extends. The angle of the stimulating lead projecting off the stimulator body allows the lead to maintain contact with the posterior maxilla as it courses from the stimulator body to the pterygopalatine fossa and reduces any stress on the stimulating lead by reducing the lead curvature. In some embodiments, the degree of the angle between the stimulator body and stimulating lead can range from between approximately 0 to 60 degrees. In yet other embodiments the stimulating lead may contain multiple compound angles with the neurostimulator, the angles may be on or off axis with the stimulator body.

In the embodiment of FIG. 2, the stimulating lead includes seven cylindrical stimulating electrodes 201 that can be configured to provide either cathodic or anodic stimulation. In this embodiment the stimulating lead comprises at least 5 stimulating cathodic electrodes, or working electrodes. The working electrodes are configured to be implanted in very close proximity to the SPG within the pterygopalatine fossa and to be used for delivering the stimulation pulses from the micro-electronics. In some embodiments, the two most proximal electrodes to the stimulator body 200a can be electronically coupled to create a larger reference or return electrode. This reference electrode can be configured as an anode and positioned on the stimulating lead such that it is the farthest electrode from the SPG.

The length and spacing of the electrodes are configured to optimize stimulation of the SPG. The average height and width of the SPG has been found to be 3.28 mm, range 2-6 mm and 1.76 mm, range 1-3 mm respectively. In some embodiments, the spacing distance between any two adjacent stimulation electrodes is no greater than 1.0 mm and each electrode is 1.5 mm in length. The electrode length and the spacing assures that at least one electrode maintains communication with the SPG. In other embodiments the electrode spacing can range from 0.3-4 mm, and the length of each electrode can range from 0.4 to 4 mm. In one embodiment, the stimulating lead and hence each electrode, is 1 mm in diameter. The diameter of the stimulating lead can be designed such that the lead passes through the lateral opening the pterygopalatine fossa, called the pterygopalatine fissure, which has been reported to be between 2-12 mm wide. In other embodiment, the diameter of the lead can range from 0.5 to 3 mm. Each stimulation electrode has a thickness of 0.1 mm; a minimum thickness of 0.05 mm is needed prevent damage during manufacturing and implantation. The stimulation electrodes can be made from 90/10 platinum/iridium alloy. However, in other embodiments the stimulation electrodes can be made from other biocompatible metallic alloys, including but not limited to platinum, platinum alloys, palladium, palladium alloys, titanium, titanium alloys, various stainless steels, or any other conductive biocompatible metals and biocompatible non-metals such as but not limited to carbon.

Figure 3A:
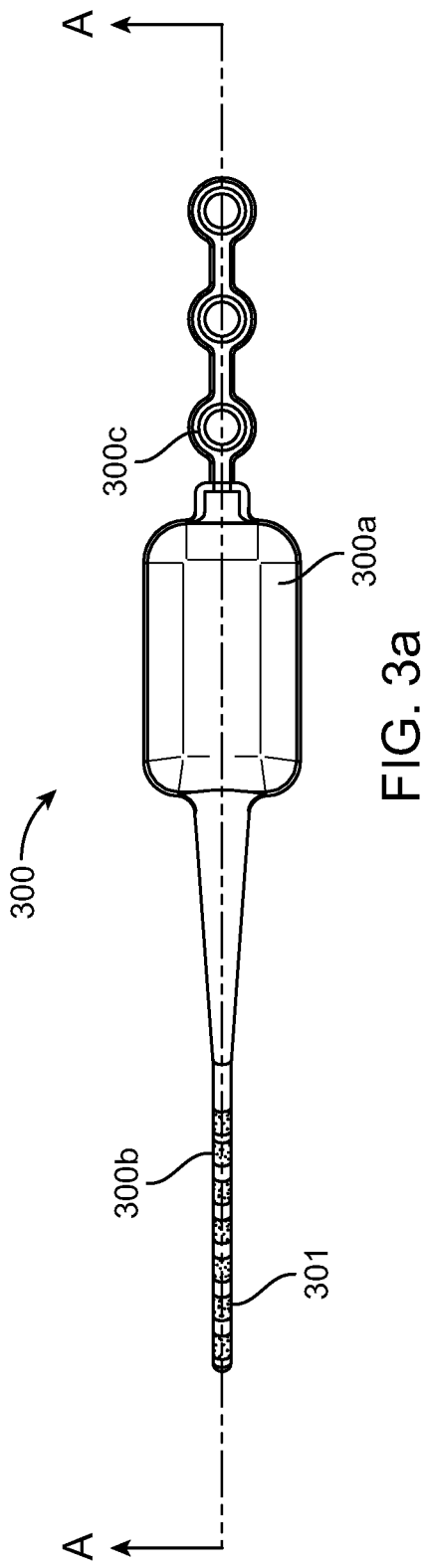
FIGS. 3a-3b are top and side section views of the neurostimulator.
Figure 3B:
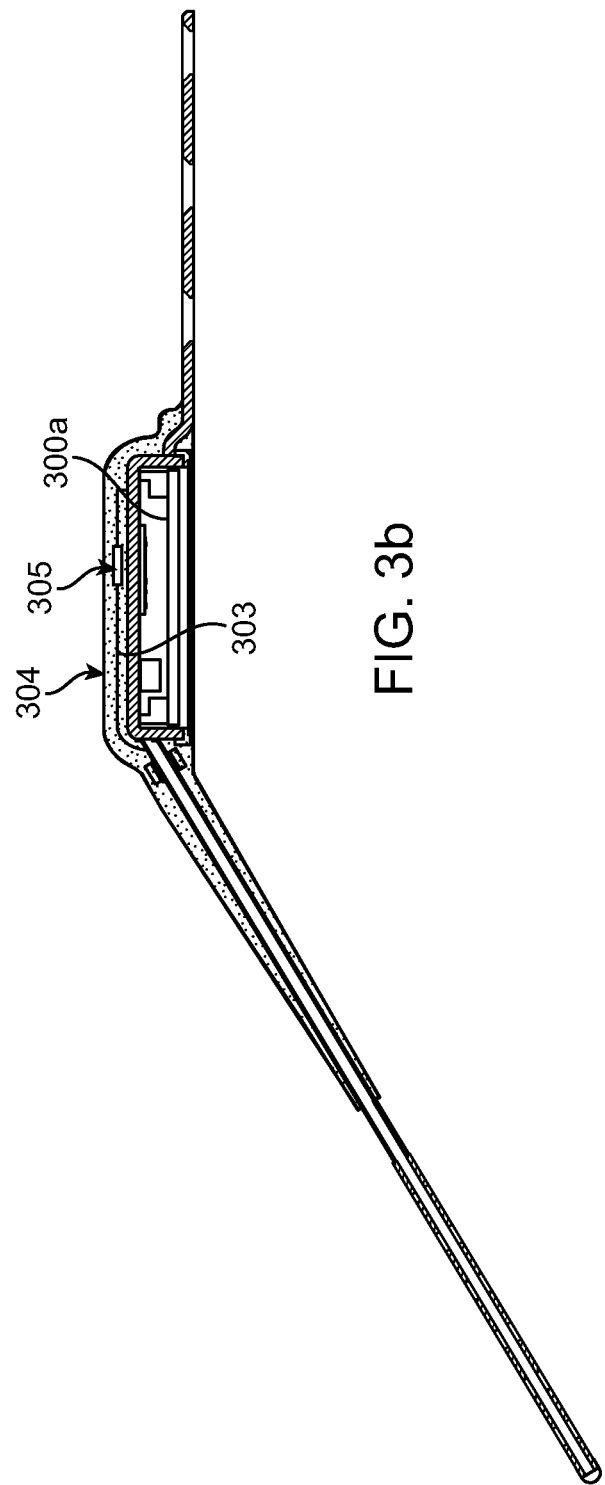

FIG. 3a is an elevated view and FIG. 3b is a sectioned side view of neurostimulator 300, and illustrates the integral design of the neurostimulator. In FIG. 3a, the neurostimulator 300 includes stimulator body 300a, integral stimulating lead 300b, which includes one or more stimulation electrodes 301, and integral fixation apparatus 300c. FIG. 3b shows a sectioned side view of the neurostimulator through the line A-A in FIG. 3a. In this embodiment, the sectioned side view shows the hermetic electronics enclosure within the stimulator body 300a, integral stimulation lead 300b, electrode wire interconnect assembly 305 and the electrode connection wires 303. Also shown in FIG. 3b is the protective (insulation) outer layer 304, which encapsulates the stimulator body and the proximal portion of the stimulation lead. The protective layer also covers the proximal portion of the stimulation lead to provide additional strain relief at the junction between the lead and the stimulator body. This layer is formed by reaction injection molding (RIM) with a biocompatible urethane and silicone co-polymer. Other encapsulations methods and materials may include potting, injection molding, casting, conformal coating, or adhering a compliant, semi-compliant, or rigid silicone rubber, epoxy, thermo set or thermoplastic polymers or combination of any of the described methods and materials around the electronic assembly, lead interconnect, and lead assembly.

Figure 4:
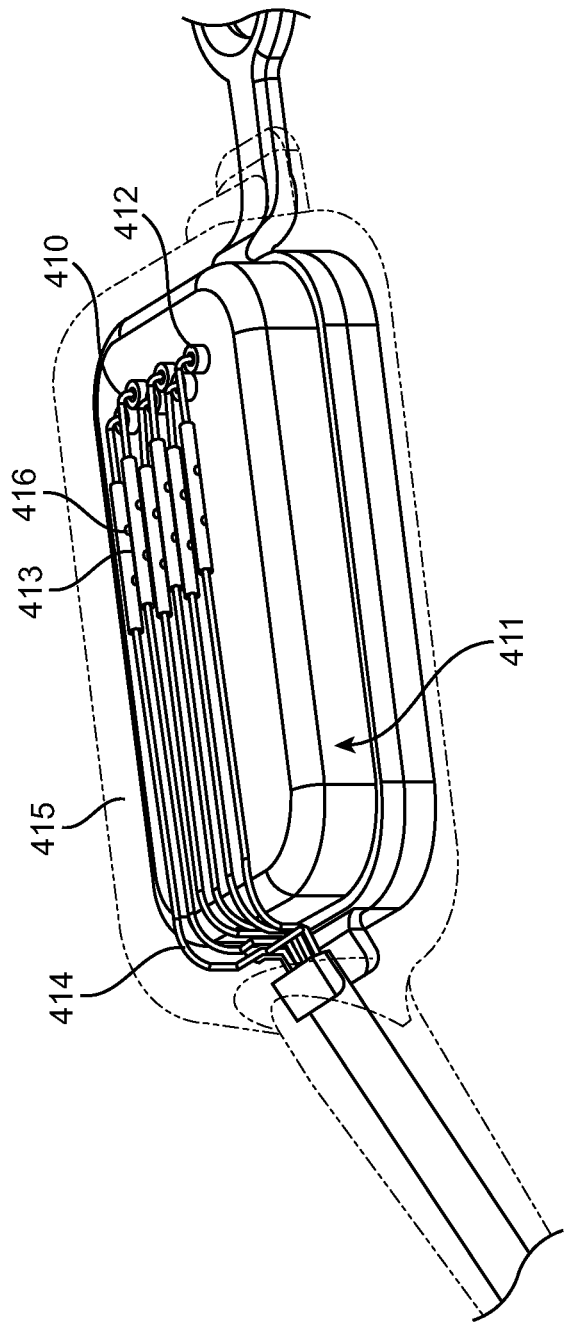
FIG. 4 is a transparent view illustrating the electrode wire interconnects.

FIG. 4 shows an enlarged detail view of the encapsulated hermetic electronics enclosure 411, feed through assembly and interconnect assembly. The feed-through wires 410 projecting from the upper surface of the hermetic electronic enclosure 411 can be bonded to the enclosure. In some embodiments, the feed-through wires are brazed onto the enclosure using gold braze 412. In other embodiments the feed-through wires can be adhered using a glass frit to the enclosure or otherwise molded or bonded to the enclosure. The feed-through wires can be served upward and then down along the enclosure toward the stimulation lead and connected to the electrode wires 414. In some embodiments, a platinum/iridium tube 413 is used to connect the electrode wires to the feed-through wires. The proximal segment of the platinum/iridium tubing can be crimped onto the feed-through wires and the distal end of the tubing can be crimped to the electrode wires 414. The platinum/iridium tubing includes at least two witness holes 416. These witness holes allow the operator to verify that the wires are appropriately placed prior to applying the crimp. In other embodiments the platinum/iridium tubing can be resistance welded; laser welded, brazed, or otherwise secured using epoxy or other conductive adhesives to the feed-through and electrode wires.

FIG. 4 also shows the outer protective encapsulation layer (in transparency). In one embodiment, the outer protective layer is a copolymer; a blend of biocompatible urethane and silicone co-polymer uniquely compounded to provide superior adhesion to the substrate while providing a tissue friendly interface. The protective layer can be molded over the stimulator body and a portion of the stimulating lead using a reaction injection molding (RIM) process. The material can be stable, biocompatible, resistant to oxidation and have increased mechanical properties compared to other polyurethanes and silicones. The protective layer is designed to provide electrical isolation between exposed conductors as well as a primary biocompatible interface between the tissue and the implanted device. The use of this material to surround the electrode wire interconnect assembly to the feed-through assembly provides stability and electrical insulation to each interconnection. The material can also be molded onto a proximal portion of the stimulation lead to act as a strain relief.

Figure 5:
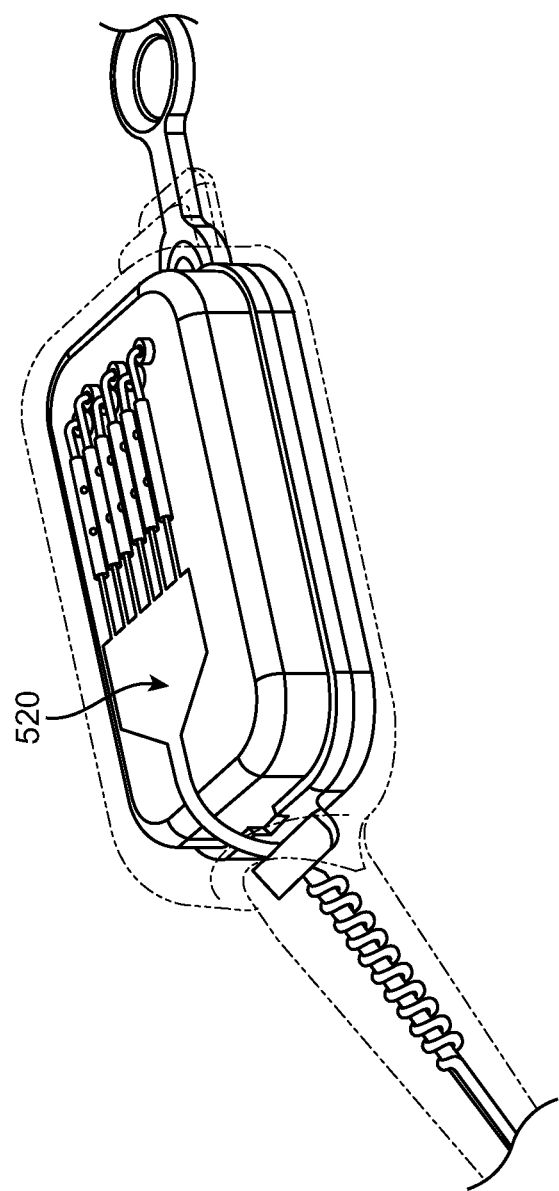
FIG. 5 is a transparent view illustrating an electrode flex circuit interconnect.

FIG. 5 illustrates an alternative embodiment of an electrode wire to feed-through interconnect system similar to the embodiment described above, except that each electrode is connected to the feed-through assembly using an organic thin-film flex circuit 520. The flex circuit can comprise of a polyamide film with printed trace lines made of a conductive material such as gold. In one embodiment, the flex circuit contains at least six trace lines printed on the polyamide film with each trace line corresponding to one electrode. In another embodiment, the polyamide film is expanded near the interconnect assembly, such that the printed trace lines are equally spaced with the feed-through assembly wires. Then each trace line on the polyamide film is extended off the film like a comb with individual fingers, each finger representing on printed trace line. Each trace can then be crimped onto the feed-through assembly wires as described above. The polyamide film can be narrowed once it enters into the stimulating lead assembly. In one embodiment, the narrowed film is no wider than 0.5 mm, such that the film is smaller than the diameter of the lead assembly (e.g., 1.0 mm). In one embodiment, the polyamide film that comprises the flex circuit is 0.1 mm thick, however in other embodiments the flex circuit can be approximately 0.05 to 0.5 mm thick. In other embodiments, the flex circuit can take on the shape needed to facilitate the interconnection between the stimulation electrodes and the feed-through assembly.

Figure 6:
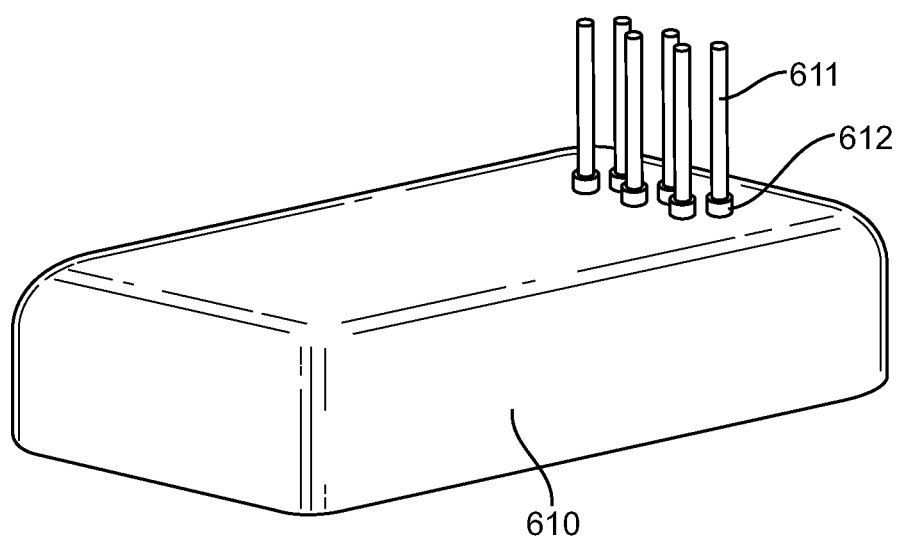
FIG. 6 is an isometric view of a feed-through interconnect embodiment.

In one embodiment, as shown in FIG. 6, the electronics enclosure 610 and integral feed-through wires 611 are shown and include an additional protrusion feature 612 in the feed-through assemblies. The protrusion feature is used to increase the surface distance between each of the monolithic feed-through wires and provide a larger surface area for increased adhesion of the copolymer. Once the outer protective layer is molded onto the electronics enclosure it provides stability and protects the electrical connections between the feed-through wires and the electrode wires. If fluid ingress occurs, coupled with the copolymer delaminating, the increased surface distance (i.e., the electrical path) between electrodes will help prevent electrical shorting. In one embodiment, the protrusion features extend above the surface of the electronics enclosure by approximately 0.25 mm. In other embodiments, the protrusions can extend between 0.1 to 0.5 mm above the enclosure. Also shown in FIG. 6, is a staggered configuration of the feed-through assemblies. Due to size constraints on the electronic enclosure, the feed-through assemblies may not be able to be arranged in a linear fashion without unintended electrical shorting between two adjacent feed-through assemblies. By staggering the feed-through assemblies, an increased number of feed-through wires can be used and the distance between adjacent feed-through assemblies could be increased, reducing the risk of electrical shorting.

Figure 7:
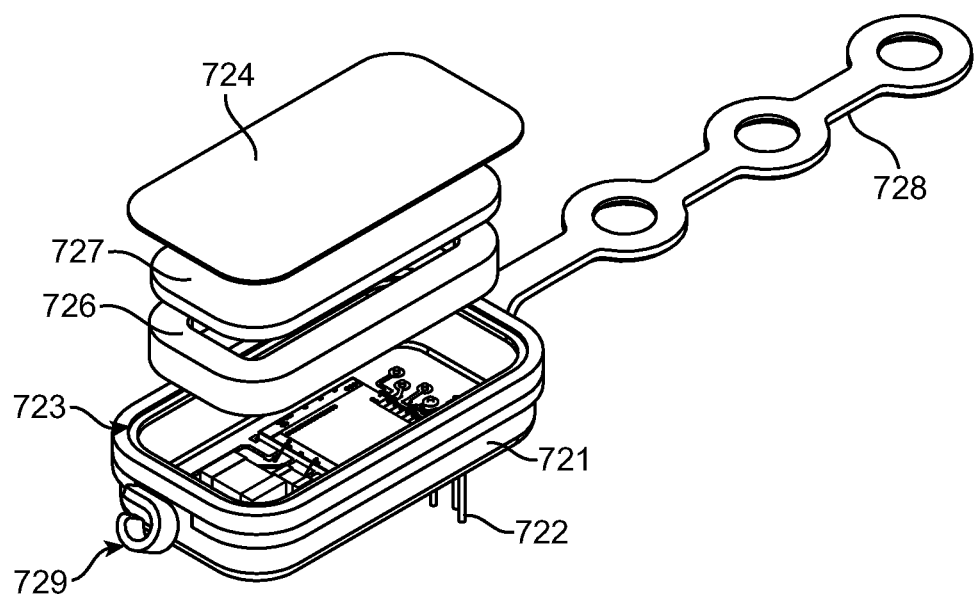
FIG. 7 is an exploded view of the neurostimulator's electronics enclosure.

FIG. 7 is an isometric exploded view of a hermetic electronics enclosure of a neurostimulator. In this embodiment, the hermetic enclosure comprises a substrate and monolithic feed-through 721, a bezel 723 and a lid 724. The hermetic enclosure houses the micro-electronic assembly, an inductive coil 726 and a ferrite core 727. In one embodiment, the substrate is manufactured from stabilized zirconium oxide and the feed-through wires are gold brazed into place and are manufactured from platinum-iridium (80/20). In other embodiments, the substrate and integral monolithic feed-through assembly 721 can be manufactured from one of many ceramic materials, including, but not limited to aluminum oxide, transparent polycrystalline aluminum oxide, stabilized zirconium oxide, aluminum nitride, and silicon nitride. The substrate and monolithic feed-through assembly can be produced using a variety of manufacturing methods including but not limited to post sintering machining, green form pressing and sintering, and injection molding and sintering.

In one embodiment, the bezel 723 and the lid 724 can be manufactured using a high resistance, biocompatible metal such as commercially pure or alloyed titanium. In other embodiments, the bezel can be made out of but not limited to other materials including corrosion resistant stainless steels, refractory's such as aluminum oxide, transparent polycrystalline aluminum oxide, stabilized zirconium oxide, aluminum nitride, and silicon nitride or glass fit.

In one embodiment, the bezel 723 is brazed at the location to the mating edge of the ceramic substrate and monolithic feed-through assembly using pure gold braze. This braze provides a gas tight seal between the bezel and the ceramic substrate of the electronics enclosure. The bezel also exhibits recessed self-alignment nesting features suitable to receive and accommodate the lid 724, which is welded to the bezel providing another gas tight seal at location between the bezel and the lid. The bezel is brazed on the ceramic substrate prior to populating the electrodes within the substrate. By doing so, the titanium lid can be welded onto the titanium bezel after the electronics assembly has been populated within the substrate. The welding between the bezel and the lid can be a low temperature process, which does not affect the electronics within the enclosure. However, if the bezel is not used, the lid would need to be brazed onto the substrate, which is a high temperature process. The high temperature process would adversely affect the electronics. The gold braze between the substrate and the bezel can be done prior to populating the electronics within the substrate allowing a lower temperature weld to be done between the lid and the bezel after populating the electronics.

Referring to FIG. 7, the electronics enclosure can house a micro-electronics assembly, an inductive coil 726 and a ferrite core 727. In this embodiment the inductive coil is connected and bonded into the electronics enclosure and used to inductively receive power and provide bi-directional communication with an external controller (not shown). The inductive coil can be configured such that when implanted within the neurostimulator at a depth of 1-3 cm, the inductive coil can still receive power and communicate with the external controller. The inductive coil can be part of an RC (resistor-capacitor) circuit designed to resonate between 120 and 130 kHz. In one embodiment, the inductive coil resonates via 2.7 to 3.3 nF capacitor. The coil can be 200 turns of 41 gauge bondable solid core magnetic wire and wound into a rectangular orientation, 11.47 mm long by 5.47 mm wide, for example. In one embodiment, the thickness of the coil is 1.5 mm. In other embodiments, the coil is configured such that it includes a step on the inner surface. This step allows for the coil to sit flat on a specific surface of the ceramic substrate and clear the protrusions of the feed-through wires on another portion of the inside surface of the ceramic substrate. The step in the coil can increase the number of turns that can be allowed to fit into the electronics enclosure. The increased number of turns allows for greater distance in which the coil can be externally powered, thus allowing for a greater distance over which bi-directional communication can occur. Additionally, in other embodiments, the length, width and thickness of the coil can be adjusted to fit into the electronics enclosure and configured such to optimize the power transfer and communication distances. The ferrite core can be bonded into the top side of the inductive coil and used to align the magnetic flux to optimize energy transfer. The micro-electronics, inductive coil and ferrite core are all contained within the electronics enclosure and hermetically sealed using a titanium lid.

The hermetic electronics enclosure also supports an integral fixation apparatus 728. The fixation apparatus as described above can be fixed to the enclosure, and in one embodiment the fixation apparatus is laser welded to the enclosure. In other embodiment the fixation apparatus can be bonded using standard biocompatible adhesives, or otherwise mechanical attached, e.g., swage or press fit to the hermetic enclosure. Additionally, the fixation apparatus includes an additional routing feature 729 located on the distal side of the stimulator body. In one embodiment, the routing feature is made from the same titanium as the fixation mini-plate and is configured to curve around the electrode wires as they pass from the stimulating lead to the stimulator body. The electrode wires are guided through the routing feature on the fixation apparatus, where they can be organized and crimped to the feed-through wires on the electronics enclosure.

Figure 8:
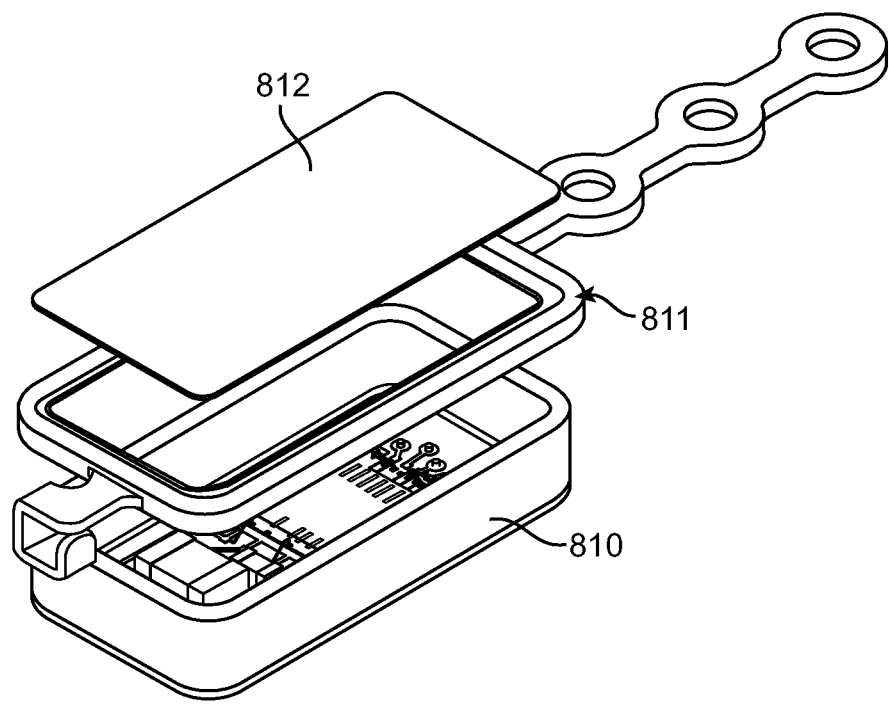
FIG. 8 is an exploded view of an electronics enclosure embodiment.

In an alternative embodiment, as illustrated in FIG. 8, an isometric exploded view of the hermetic electronics enclosure 810 including the integral fixation apparatus which includes the bezel 811 and a lid 812 is shown without the stimulation lead assembly and protective outer layer. In this embodiment, the fixation apparatus is integral to the bezel. The integral bezel and fixation apparatus are then brazed onto the ceramic electronics enclosure.

In this embodiment, the braze bezel 811 also exhibits a recessed self-alignment nesting features suitable to receive and accommodate the lid 812 which can be welded to the braze bezel providing a gas tight seal between the braze bezel and the lid, as shown in FIG. 8.

Figure 9:
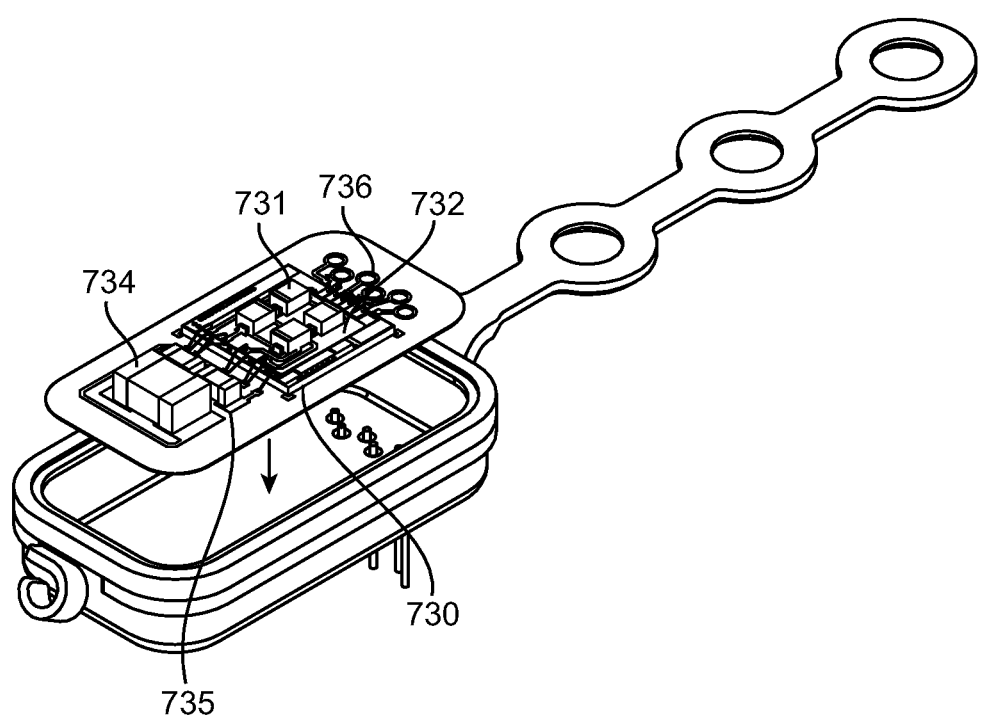
FIG. 9 is an isometric view of the electronics enclosure embodiment.

FIG. 9 illustrates one embodiment of a three-dimensional micro-electronics assembly. In this embodiment the micro-electronics assembly comprises of an Application Specific Integrated Circuit (ASIC) 730, a diode array 731, a diode array interposer 732, an ASIC interposer, and discrete components including but not limited to a resonating capacitor 734 and a smoothing capacitor. In one embodiment, the diode array is soldered or conductive adhesive bonded onto an organic or ceramic interposer. The diode interposer provides a conductive patterned electrical circuit between the arranged diodes. In one embodiment, the diode interposer is then adhesive bonded to the upper surface of the ASIC. The diode array rectifies the alternating current coming from the RC circuit which is then used to power the ASIC.

As shown in FIG. 9, the AISC with the bonded diode array interposer can be adhesive bonded onto a second organic or ceramic interposer. In one embodiment the ASIC is wire-boned using gold ball bonding or wedge bonding between exposed circuit pads on the interposer and exposed pads on the ASIC. The ASIC interposer provides a patterned electrical circuit between discrete components and the ASIC including but not limited to a resonating capacitor and smoothing capacitors. The discrete components are soldered or conductive adhesive bonded to the ASIC interposer. In one embodiment, the micro-electronic assembly, including the ASIC 730, diode array 731, diode array interposer 732, ASIC interposer, resonating capacitor 734 and smoothing capacitor, is bonded or adhered to the lower surface of the brazed hermetic ceramic electronics enclosure, or alternatively, is printed directly into the brazed hermetic ceramic electronics enclosure.

In one embodiment, as shown in FIG. 9, the ASIC interposer contains one or more apertures 736, which are metalized annular rings, to receive the exposed ends of the conductive feed-through pins. The electrical connection between the ASIC interposer and the feed-through wire is done using conductive epoxy. In other embodiments the electrical connections between the ASIC interposer and the feed-through wires can be done using traditional wire-bonding techniques, or soldering the metalized annular rings around the aperture to the feed-through pins.

Figure 10:
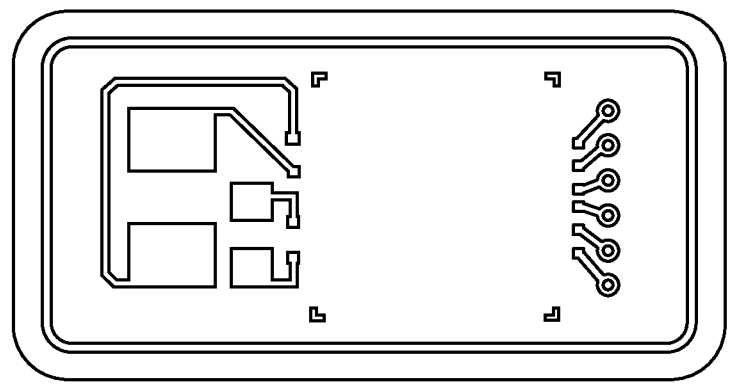
FIG. 10 is a top down view of the neurostimulator's electronics and enclosure.

In other embodiments, as illustrated in FIG. 10, the ASIC interposer described above is metalized directly onto the inner bottom surface of the ceramic substrate. The metalized patterned electrical circuit is metalized using thick film, or a sputtered metal deposition to impose the circuit pattern on the substrate, in which to affix electronic components. Metalizing the substrate facilitates communication between the assembled components and the outside environment at the location where the metalized substrate interfaces with the monolithic feed-through using wires brazed into the enclosure. In one embodiment, the metalized thick film or sputter is a few angstroms thick, and more specifically a 2000 angstrom thick layer of platinum and gold is laid directly on the ceramic substrate to create the patterned electrical circuit.

Figure 11:
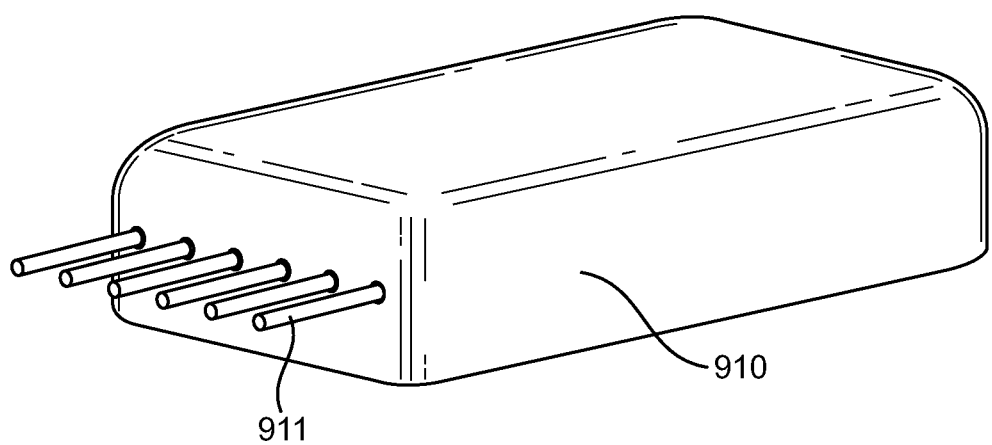
FIG. 11 is an isometric view of a feed-through interconnect embodiment.

In other embodiments, as illustrated in FIG. 11, the position of the monolithic feed-through assemblies 911 on the ceramic substrate 910 can protrude through the distal wall of the ceramic substrate. In this embodiment, the substrate can be manufactured from stabilized zirconium oxide and the feed-through pins can be gold brazed into place and can be manufactured from platinum-iridium (80/20). In various other embodiments the integral substrate and monolithic feed-through assembly may be manufactured from one of many ceramic materials, including, but not limited to aluminum oxide, transparent polycrystalline aluminum oxide, aluminum nitride, and silicon nitride. Also the electronics enclosure, integral substrate and monolithic feed-through assembly can be produced using a variety of manufacturing methods including but not limited to post sintering machining, green form pressing and sintering, and injection molding and sintering. The pins may also be manufactured from platinum or other platinum alloys, palladium, titanium, or stainless steel.

Figure 12:
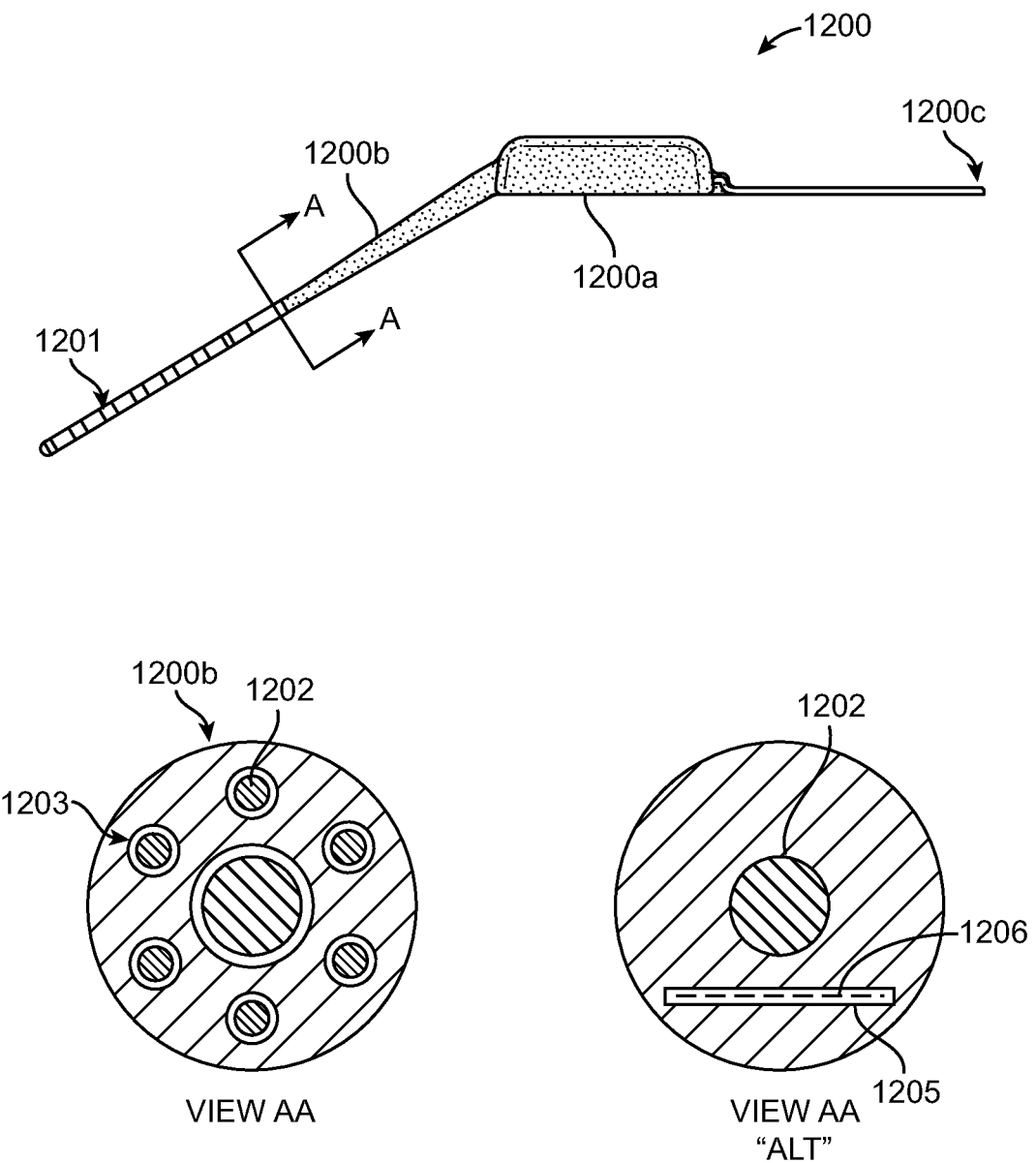
FIG. 12 illustrates embodiments of the lead cross-sections.

FIG. 12 illustrates a side view of one embodiment of the neurostimulator 1200, which can comprise of a stimulator body 1200a, a stimulation lead 1200b, which contains one or more stimulation electrodes 1201, and an integral fixation apparatus 1200c. FIG. 12 also shows two embodiments of the cross-section through the diameter of the stimulation lead 1200b. In one embodiment, the cross-section view AA in FIG. 12, the electrode wires or conductors 1202 that are electrically connected to the feed-through assemblies on the electronic enclosure for each electrode are discrete, independently insulated conductor wires serviced within individual lumens 1203 in the integral stimulation lead 1200b. In one embodiment the stimulation lead is manufactured using a multi-lumen extruded copolymer. The copolymer used in the extruded multi-lumen lead is very similar to the copolymer used in the outer protective (insulating) layer that covers the stimulator body and a portion of the stimulation lead. In this embodiment, the copolymer used has an increased hardness compared to the outer protective layer copolymer. In one embodiment, the conductive electrode wires can be made of stranded platinum-iridium (90/10) wire with a diameter of 0.1 mm. In other embodiments the conductive wire can be made from but not limited to stranded or finely bundled cable assemblies or in alternate embodiments a solid wire. The conductive electrode wires can be manufactured from but not limited to platinum, platinum-iridium alloy, MP35N or a variation of MP35N including a DFT, drawn and filled tubing, stainless steel, gold, or other biocompatible conductor materials. The center lumen in the cross-section can includes a malleable wire segment made from platinum-iridium (90/10) with a diameter up to 0.4 mm. The malleable wire segment in the center lumen, in one embodiment, can be made from but not limited to platinum, platinum-iridium alloy, MP35N or a variation of MP35N including a DFT. The additional of the malleable wire or other stiffening mechanism to the center lumen, in one embodiment, provides the stimulation lead assembly with added mechanical properties, such as, increasing the linear stiffness of the lead and providing increased flex fatigue properties to the entire lead assembly. The increase in the linear stiffness of the stimulation lead is needed to ease the implantation of the neurostimulator. For example, the stimulation lead having a malleable wire can be configured to have the rigidity to penetrate and dissect through blunt tissue, but remain malleable enough to be bent into a shape to conform to the target anatomy.

In one embodiment, the neurostimulator is configured to be implanted within the pterygopalatine fossa, a deep structure located behind the base of the nose, and just anterior the skull base. As described in U.S. Patent Application No. 61/145,122 to Papay, which is incorporated herein by reference, the intended implantation of the neurostimulation into the pterygopalatine fossa is through a trans-oral approach using a custom implantation tool to aid in the placement of the neurostimulator. An increased linear stiffness of the stimulation lead will greatly add to the ease of the implantation. Additionally, as referenced the Papay application, the intended implant location of the stimulator body is on the posterior maxilla with the stimulation lead extending to the pterygopalatine fossa along the posterior maxilla. In this location, the stimulator body and the stimulator lead will be subject to compressive forces due to the motion of the surrounding anatomy from movements of the lower jaw. Thus increasing the flex fatigue resistance of the stimulation lead will increase the life time of the chronically implanted neurostimulator.

Referring still to FIG. 12, in other embodiments, the center lumen of the stimulation lead may not be used to support a wire segment. In one embodiment, a supporting wire 1202 may be floating within the lumen or directly contacting the stimulation lead over-molding encapsulation, as shown in the cross-sectional view AA "ALT" on the right in FIG. 12. This view is in reference to the thin film flex circuit embodiment described above. In this embodiment, the flex circuit 1205 is suspended within the encapsulation of the stimulation lead. Also as discussed above the flex circuit contains one or more printed conductive traces 1206 that electrically connect each electrode to the feed-through assembly on the electronics enclosure.

Figure 13:
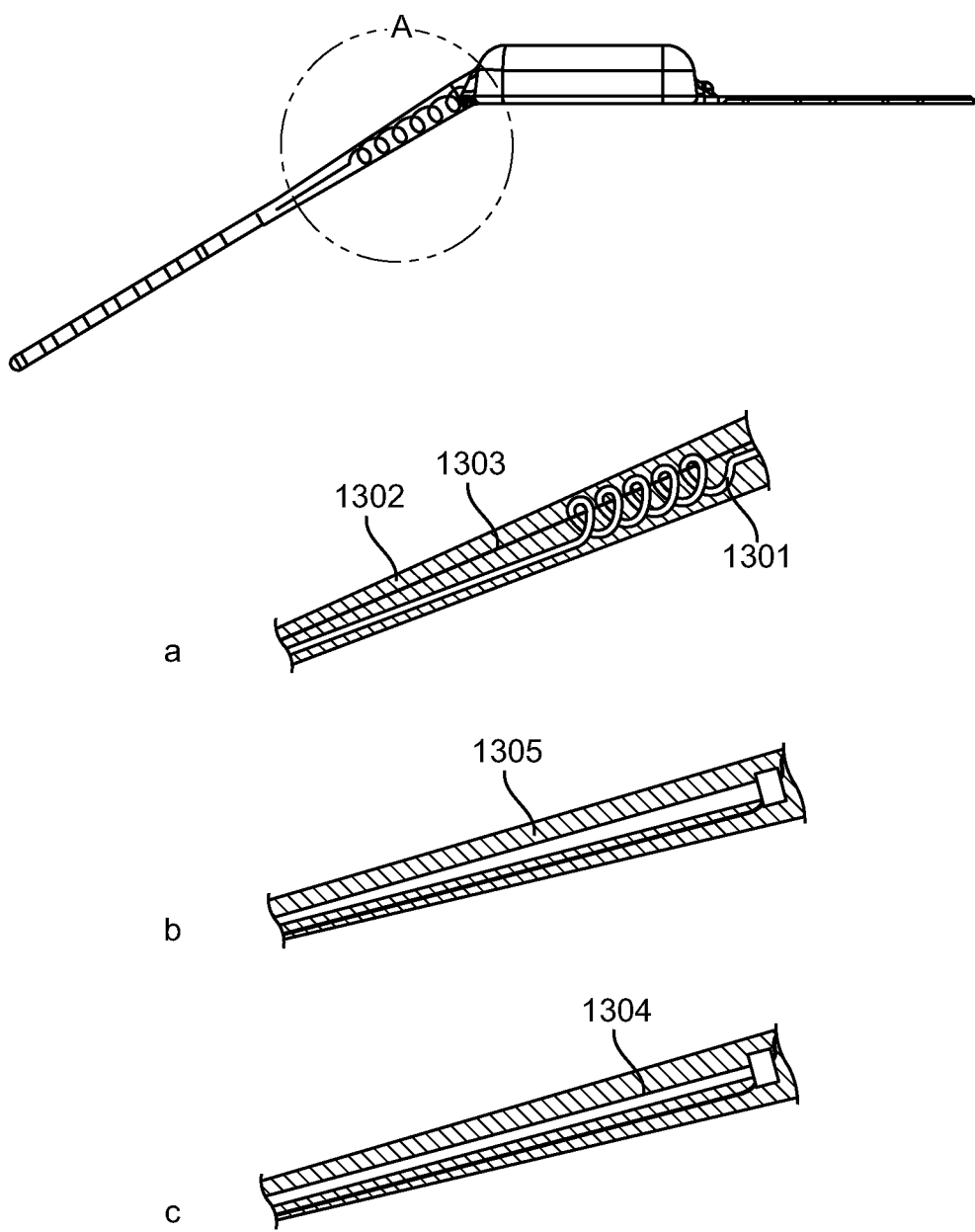
FIG. 13 illustrates axial cross-sectional insets of lead embodiments.

FIG. 13 shows additional alternate embodiment of a neurostimulator in side view. FIGS. 13a, b, and c also show three sectional details of the neurostimulator illustrating alternative embodiments that include methods to facilitate mechanical manipulation and resistance to fatigue in-vivo. FIG. 13a shows one embodiment in which a coiled wire 1301 may be added to the proximal portion of the stimulation lead as it mates with the stimulator body. In this embodiment the coiled wire can be manufactured from a straight or partially coiled wire made of a highly malleable biocompatible alloy such as palladium, platinum, or annealed platinum. In this embodiment the coiled wire is configured such that the stimulation lead has optimal resistance to fatigue in vivo. To optimize the flex resistance of the inserted coil within the stimulation lead the following parameters can be adjusted; the diameter of the wire, the outer diameter of the coil, pitch of the coil, and the number of turns in the coil. In one embodiment, the coil was manufactured using a palladium wire with a diameter of 0.25 mm, and manufactured into a coil with 5 turns, a coil pitch of 1.0 mm, and an outer diameter 1.0 mm. The coil is then suspended within the over-mold material 1302 of the lead as described above. In this embodiment the electrode wires 1303 that electrically connect the electrodes to the feed-through interconnects transverse through the center of the coiled wire segment.

In alternate embodiments, as shown in FIG. 13c, the supporting wire 1304 can be straight and be manufactured from more rigid materials such as titanium, stainless steel, or nitinol. In other embodiment, a combination between the more rigid straight section of the wire and a coiled wire can be employed. In this embodiment the coiled/straight material can be manufactured using the one wire or using discrete wires for each segment of the supporting wire. In this embodiment, the supporting wire can be manufactured from highly malleable biocompatible alloy such as palladium, platinum, or annealed platinum allow or from more rigid materials such as annealed titanium, stainless steel, nitinol, or any combination thereof.

In yet another alternative embodiment, as shown in FIG. 13b, a tapered supporting wire 1305 can be used. In this embodiment, a tapered wire with a heaver diametric cross-section proximally and tapering to a finer cross-section distally is used to provide support to the stimulation lead. In one embodiment, the tapered wire may be manufactured from either highly malleable biocompatible alloy such as palladium, platinum, or annealed platinum allow. In alternate embodiments the wire can be manufactured from more rigid materials such as annealed titanium, stainless steel, or nitinol. In one embodiment, the tapered supporting wire can start at a diameter of 0.5 mm and taper to a diameter 0.1 mm at the distal portion of the wire. In other embodiments, the tapered wire can start with a diameter between 0.5 to 0.8 mm and taper to a diameter of 0.4 to 0.05 mm. The tapered support wire can provide increased mechanical stability and improved flex resistance at the junction between the stimulation lead and the stimulator body, as well as provide increased bending at the distal tip of the stimulation lead over a straight non-tapered supporting wire.

Figure 14:
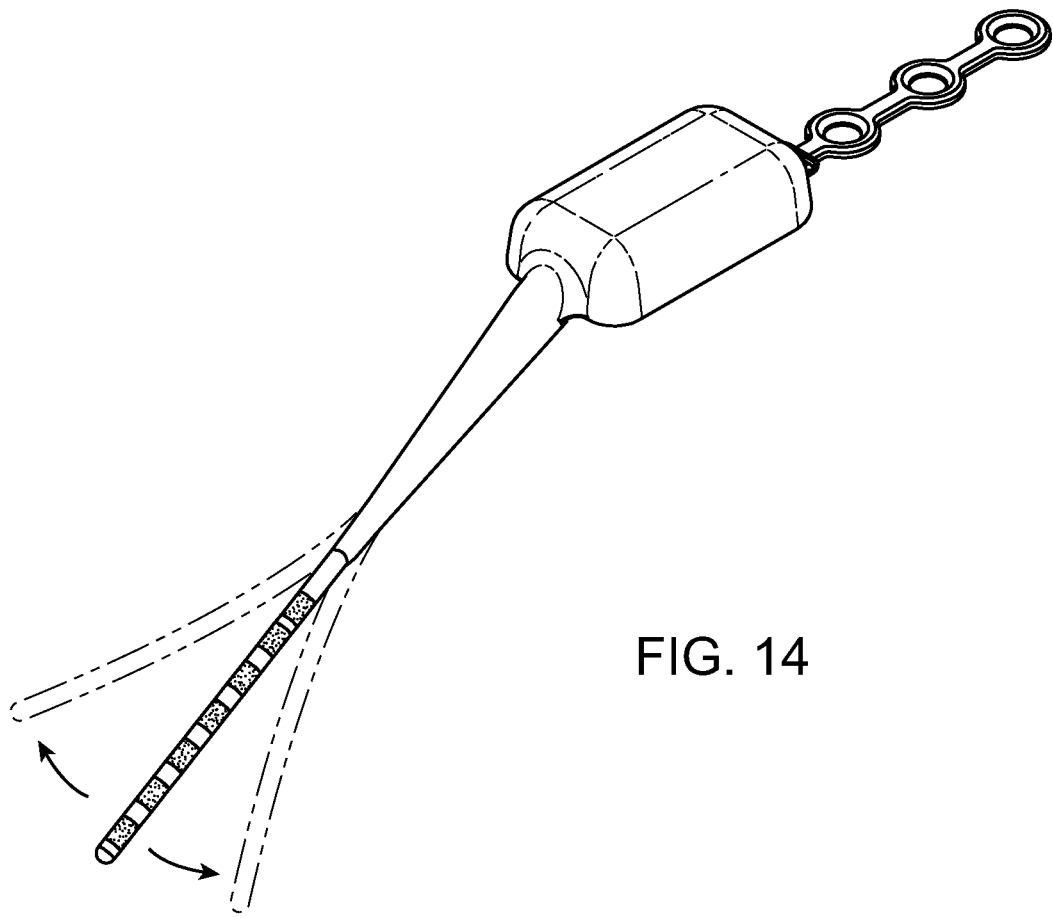
FIG. 14 is an isometric view of an embodiment of a bendable lead.
Figure 15:
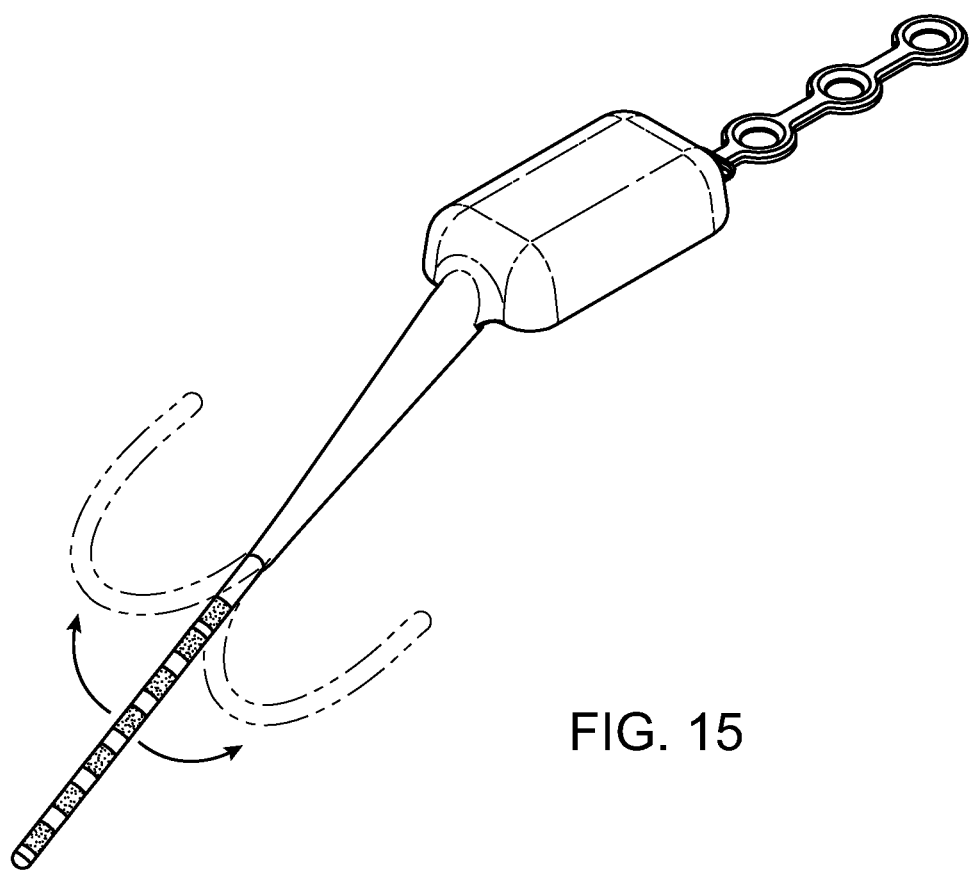
FIG. 15 is an isometric view of an embodiment of a bendable lead.
Figure 16:
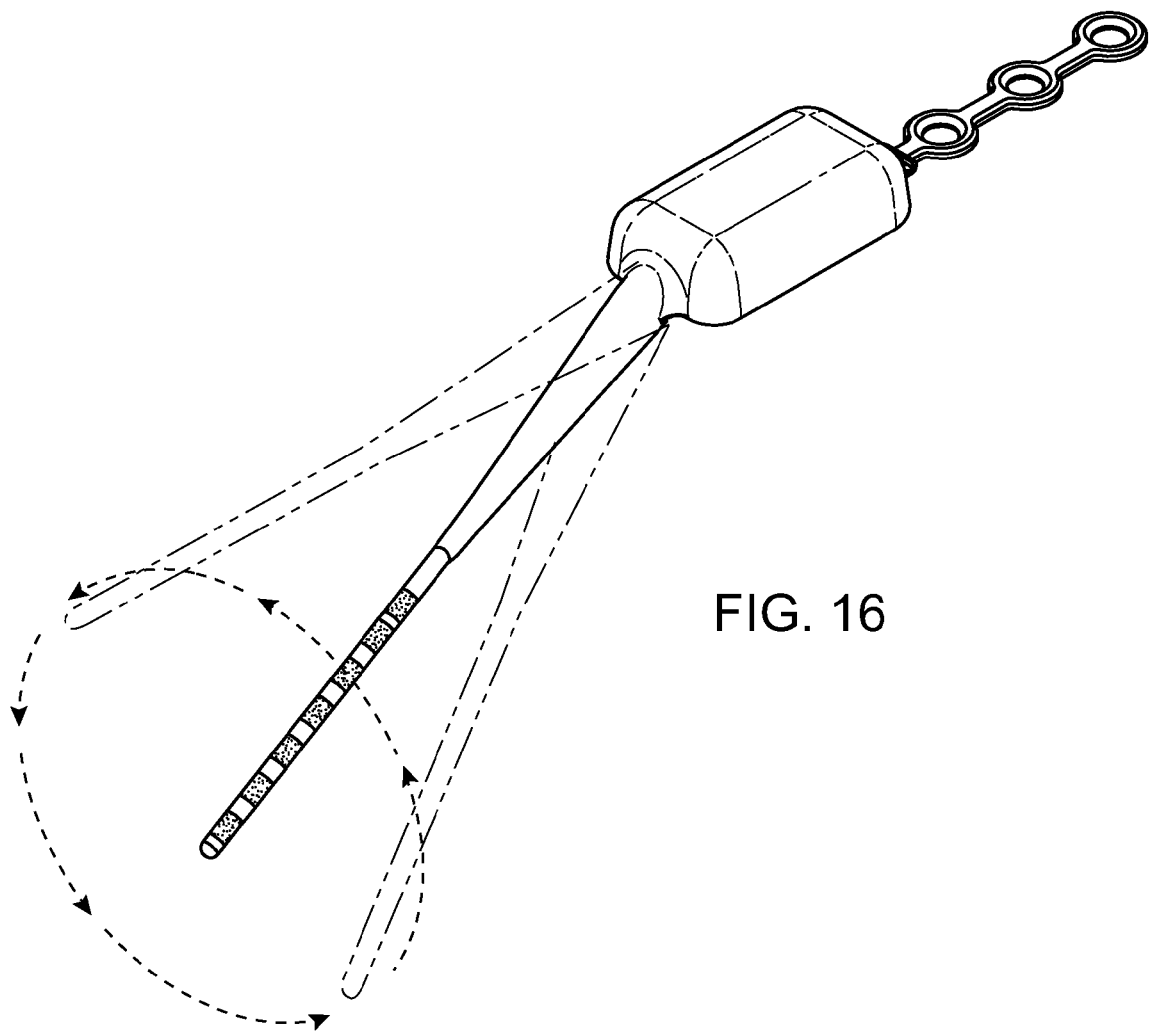
FIG. 16 is an isometric view of an embodiment of a bendable lead.

FIGS. 14, 15 and 16 illustrate the ability of the integral stimulation lead, in one or more embodiments to be bent and/or shaped into any direction and the ability to retain the directional manipulation made to the stimulation lead during implant. FIGS. 14 and 15 depict the ability of the distal stimulation lead to be bent in any direction to accommodate the needed implantation of the neurostimulator. FIG. 16 depicts the ability of the entire stimulation lead to be manipulated into any angle compared to the stimulator body and retain that position during implantation.

It will be appreciated by persons skilled in the art that the present invention is not limited to what has been particularly shown and described. Rather, the scope of the present invention includes both combinations and sub-combinations of the various features described, as well as variations and modifications thereof that are not in the prior art, which would occur to persons skilled in the art upon reading the foregoing description.

What is claimed is:

1. An implantable medical device configured for delivery of electrical stimulation to the Sphenopalatine Ganglion (SPG), comprising:
    an electronics enclosure;
    a substrate housed in the electronics enclosure;
    a monolithic feed-through coupled to the electronics enclosure and the substrate;
    a stimulation lead having at least one electrode coupled to the electronics enclosure with at least one electrode wire; and
    a platinum/iridium tubing having at least one witness hole, the platinum/iridium tubing being configured to connect the at least one electrode wire to the monolithic feed-through.

2. The implantable medical device of claim 1 further comprising a fixation apparatus attached to the electronics enclosure.

3. The implantable medical device of claim 2 wherein the fixation apparatus comprises at least one preformed hole configured to accept a bone screw.

4. The implantable medical device of claim 2 wherein the fixation apparatus is malleable and configured to be formed around the zygomaticomaxillary buttress.

5. The implantable medical device of claim 1 wherein the electronics enclosure comprises an ASIC, an inductive coil, and a diode array.

6. The implantable medical device of claim 1 wherein the implantable medical device is sized and configured for implantation into the pterygopalatine fossa.

7. The implantable medical device of claim 1 wherein the implantable medical device is sized and configured for implantation on the posterior maxilla.

8. The implantable medical device of claim 1 wherein the stimulation lead is constructed to an angle off an axis of the electronics enclosure.

9. The implantable medical device of claim 8 wherein the angle is approximately 0 to 60 degrees.

10. The implantable medical device of claim 8 wherein the angle is approximately 30 degrees.

11. The implantable medical device of claim 8 wherein the implantable medical device is configured to lay flat against the posterior maxilla, and the stimulation lead is angled so as to maintain contact with the posterior maxilla as it extends to the pterygopalatine fossa.

12. The implantable medical device of claim 8 wherein the stimulation lead is sized and configured to pass through a lateral opening of the pterygopalatine fossa.

13. The implantable medical device of claim 12 wherein a diameter of the stimulation lead is approximately 2-12 mm.

14. The implantable medical device of claim 1 further comprising a thin-film flex circuit configured to connect the at least one electrode wire to the monolithic feed-through.

15. The implantable medical device of claim 1 further comprising a protrusion feature disposed on the monolithic feed-through.

16. The implantable medical device of claim 1 further comprising an inductive coil configured to receive power and communication from an external controller at a depth of approximately 1-3 cm.

17. The implantable medical device of claim 1 wherein the electronics enclosure comprises an ASIC printed on the electronics enclosure.

18. The implantable medical device of claim 17 further comprising at least one annular ring coupled to the electronics enclosure and configured to receive exposed ends of the monolithic feed-through.

19. The implantable medical device of claim 1 further comprising a stiffening mechanism configured to increase the linear stiffness of the stimulation lead.

20. The implantable medical device of claim 19 wherein the stiffening mechanism comprises a malleable wire.

21. The implantable medical device of claim 19 wherein the stiffening mechanism comprises a coiled wire.

22. The implantable medical device of claim 19 wherein the stiffening mechanism comprises a tapered supporting wire.

* * * * *